United States Patent
Tia et al.

(10) Patent No.: US 9,841,417 B2
(45) Date of Patent: Dec. 12, 2017

(54) MICROFLUIDIC DEVICES AND METHODS FOR ASSAYING A FLUID SAMPLE USING THE SAME

(71) Applicant: The Regents of the University of California, Oakland, CA (US)

(72) Inventors: Samuel Tia, Berkeley, CA (US); Amy E. Herr, Oakland, CA (US); Mei He, Albany, CA (US); Dohyun Kim, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 70 days.

(21) Appl. No.: 13/630,240

(22) Filed: Sep. 28, 2012

(65) Prior Publication Data

US 2013/0266956 A1 Oct. 10, 2013

Related U.S. Application Data

(60) Provisional application No. 61/541,866, filed on Sep. 30, 2011.

(51) Int. Cl.
G01N 33/543 (2006.01)
G01N 21/64 (2006.01)
(Continued)

(52) U.S. Cl.
CPC ....... *G01N 33/543* (2013.01); *G01N 21/6428* (2013.01); *G01N 33/54366* (2013.01);
(Continued)

(58) Field of Classification Search
CPC ........... G01N 27/447; G01N 27/44756; G01N 27/44773; G01N 27/44791; G01N 30/00;
(Continued)

(56) References Cited

U.S. PATENT DOCUMENTS

| 5,407,546 A | 4/1995 | Schickle |
| 5,420,016 A | 5/1995 | Boguslaski et al. |

(Continued)

FOREIGN PATENT DOCUMENTS

| JP | 2004-61319 A | 2/2004 |
| JP | 2004109062 | 4/2004 |

(Continued)

OTHER PUBLICATIONS

Fonslow et al., "Free-Flow Electrophoresis on an Anodically Bonded Glass Microchip", Anal. Chem., Sep. 1, 2005, vol. 77(17), pp. 5706-5710.

(Continued)

*Primary Examiner* — Rebecca Martinez
(74) *Attorney, Agent, or Firm* — Bret E. Field; Rudy J. Ng; Bozicevic, Field & Francis LLP

(57) ABSTRACT

Multi-directional microfluidic devices and methods for using the same are provided. Aspects of the present disclosure include microfluidic devices that include a chamber having a separation medium, a first binding medium, and a second binding medium. In addition, the devices include a flow field element configured to subject the chamber to two or more directionally distinct flow fields. Methods of using the devices, as well as systems and kits that include the devices are also provided. The devices, systems and methods find use in a variety of different applications, including diagnostic, research and validation assays.

29 Claims, 8 Drawing Sheets

(51) Int. Cl.
*G01N 21/05* (2006.01)
*B01L 3/00* (2006.01)
*G01N 21/03* (2006.01)

(52) U.S. Cl.
CPC .......... *B01L 3/50273* (2013.01); *G01N 21/05* (2013.01); *G01N 2021/0346* (2013.01); *G01N 2021/058* (2013.01)

(58) Field of Classification Search
CPC .......... G01N 33/543; G01N 27/44747; G01N 2030/528; B01D 57/02; B01D 61/58; B01D 63/00; B01D 2221/10; B01L 2300/0816; B01L 3/5027; B01L 2400/0421; B01L 2300/087
See application file for complete search history.

(56) References Cited

U.S. PATENT DOCUMENTS

| | | |
|---|---|---|
| 5,637,469 A | 6/1997 | Wilding et al. |
| 5,858,195 A | 1/1999 | Ramsey |
| 6,499,499 B2 | 12/2002 | Dantsker et al. |
| 6,613,581 B1 | 9/2003 | Wada et al. |
| 6,649,419 B1 | 11/2003 | Anderson |
| 6,818,112 B2 | 11/2004 | Schneider et al. |
| 6,969,452 B2 | 11/2005 | He et al. |
| 6,974,526 B2 | 12/2005 | Lee et al. |
| 7,112,444 B2 | 9/2006 | Beebe et al. |
| 7,235,389 B2 | 6/2007 | Lim et al. |
| 7,241,421 B2 | 7/2007 | Webster et al. |
| 7,641,780 B2 | 1/2010 | Lee et al. |
| 7,754,150 B2 | 7/2010 | Wada et al. |
| 7,828,948 B1 | 11/2010 | Hatch et al. |
| 8,329,016 B1 | 12/2012 | Sommer et al. |
| 2001/0041332 A1 | 11/2001 | Hillebrand et al. |
| 2002/0153046 A1 | 10/2002 | Dantsker et al. |
| 2003/0089605 A1 | 5/2003 | Timperman |
| 2003/0127331 A1 | 7/2003 | Leka |
| 2004/0112751 A1 | 6/2004 | Han et al. |
| 2004/0158890 A1 | 8/2004 | Thomashow et al. |
| 2004/0209354 A1 | 10/2004 | Mathies et al. |
| 2005/0020814 A1 | 1/2005 | Rudolph et al. |
| 2005/0106740 A1 | 5/2005 | Boyes et al. |
| 2005/0155861 A1 | 7/2005 | Guzman |
| 2005/0217996 A1 | 10/2005 | Liu et al. |
| 2005/0269267 A1 | 12/2005 | Patton et al. |
| 2006/0191792 A1 | 8/2006 | Herr et al. |
| 2006/0207880 A1 | 9/2006 | Joyce et al. |
| 2006/0211055 A1 | 9/2006 | Hafeman et al. |
| 2007/0121111 A1 | 5/2007 | Blumenfeld et al. |
| 2007/0131552 A1* | 6/2007 | Jung et al. ............... 204/456 |
| 2007/0187243 A1 | 8/2007 | Patton et al. |
| 2008/0067079 A1 | 3/2008 | Takahashi et al. |
| 2009/0071828 A1* | 3/2009 | Squires et al. .......... 204/453 |
| 2009/0194483 A1 | 8/2009 | Robotti et al. |
| 2010/0101953 A1 | 4/2010 | Yokoyama et al. |
| 2010/0108519 A1 | 5/2010 | Soper et al. |
| 2011/0177618 A1 | 7/2011 | Herr et al. |

FOREIGN PATENT DOCUMENTS

| | | |
|---|---|---|
| JP | 2005172453 | 6/2005 |
| JP | 2006-10529 A | 1/2006 |
| JP | 2006162405 | 6/2006 |
| JP | 2007139759 | 6/2007 |
| JP | 2007-518977 A | 7/2007 |
| JP | 2008128835 | 6/2008 |
| JP | 2008-537119 A | 9/2008 |
| WO | 00/73799 A1 | 12/2000 |
| WO | 02/086332 A1 | 10/2002 |
| WO | 2006/102516 A2 | 9/2006 |
| WO | WO 2010135364 A2 | 11/2010 |
| WO | 2011106693 A2 | 9/2011 |
| WO | WO 2011142781 A2 | 11/2011 |
| WO | 2012/071472 A2 | 5/2012 |
| WO | 2012/075308 A2 | 6/2012 |

OTHER PUBLICATIONS

He et al., "Microfluidic Polyacrylamide Gel Electrophoresis with in Situ Immunoblotting for Native Protein Analysis", Anal. Chem., Oct. 1, 2009, vol. 81(19), pp. 8177-8184.

Lerch et al., "Electrokinetic Fluid Control in Two-Dimensional Planar Microfluidic Devices", Anal. Chem., Oct. 1, 2007, vol. 79(19), pp. 7485-7491.

Renzi, et al., "Hand-Held Microanalytical Instrument for Chip-Based Electrophoretic Separations of Proteins", Anal. Chem., Jan. 15, 2005, vol. 77(2), pp. 435-441.

Song, et al., "Electrophoretic Concentration of Proteins at Laser-Patterned Nanoporous Membranes in Microchips", Anal. Chem., Aug. 1, 2004, vol. 76(15), pp. 4589-4592.

Zeng et al., "Microfluidic Self-Patterning of Large-Scale Crystalline Nanoarrays for High-Throughput Continuous DNA Fractionation", Angew. Chem. Int. Ed., Jul. 15, 2008, vol. 47, pp. 6388-6391.

Kim, et al., "Microfluidic Western Blotting: Cationic Surfactant Based Protein Sizing Integrated with electrostatic Immobilization", IEEE MEMS 24th International Conference, pp. 197-200 (2011).

He, et al., "Automated Microfluidic Protein Immunoblotting", Nature Protocols, vol. 5, No. 11, pp. 1844-1856 (2010).

He et al., 'Polyacrylamide Gel Photopatterning Enables Automated Protein Immunoblotting in a Two-Dimensional Microdevice' J. Am. Chem. Soc., 2010, vol. 132, pp. 2512-2513.

Subramanian, "Dye-ligand affinity chromatography: the interaction of cibacron blue F3Ga with proteins and enzymes", 1984, Critical Reviews in Biochemistry and Molecular Biology, 16(2): pp. 169-205.

Zhang et al. "High-Speed Free-Flow Electrophoresis on Chip", Anal. Chem. vol. 75, pp. 5759-5766 (2003).

Foote (2005)"Preconcentration of Proteins on Microfluidic Devices Using Porous Silica Membranes" Anal. Chem., 77(1): 57-63.

Lichtenberg (2001) "Sample preconcentration by field amplification stacking for microchip-based capillary electrophoresis" Electrophoresis. 22(2): 258-271.

Kim et al., (2012) "Electrostatic protein immobilization using charged polyacrylamide gels and cationic detergent microfluidic western blotting" *Anal. Chem.*, 84(5): 2533-2540.

Zilberstein et al. (2010) "Third generation of focusing: Gel matrices with immobilizedcation gradients" *Electrophoresis*, 31(11): 1747-1753.

Zilberstein et al. (2008) "DNA separation methodology based on charge neutralization in a polycationic gel matrix" *Anal. Chem.*, 80(13): 5032.

* cited by examiner

MICROFLUIDIC DEVICES AND METHODS FOR ASSAYING A FLUID SAMPLE USING THE SAME

INTRODUCTION

A variety of analytical techniques may be used to detect specific analytes in a given sample. For example, Western blotting can be used to detect proteins in a sample by using gel electrophoresis to separate the proteins in the sample followed by probing with antibodies specific for the target protein. Southern blotting combines transfer of electrophoresis-separated DNA fragments to a filter membrane and subsequent fragment detection by probe hybridization. Northern blotting involves the use of electrophoresis to separate RNA samples by size, and detection with a hybridization probe complementary to part of or the entire target sequence. Eastern blotting can be used to detect protein post translational modifications (PTM) by analyzing electrophoresis-separated proteins for post-translational modifications using probes specific for lipids, carbohydrate, phosphorylation or any other protein modifications. Far-Western blotting is similar to Western blotting, but uses a non-antibody protein to bind the protein of interest, and thus can be used to detect protein-protein interactions. Southwestern blotting is a technique that can be used to detect DNA-binding proteins by using gel electrophoresis to separate the proteins in a sample followed by probing with genomic DNA fragments.

Conventional blotting techniques, as discussed above, may fall short of performance needs for applications that demand either high-throughput sample analysis or operation in resource poor settings. Blotting techniques may require labor-intensive, time consuming, multi-step procedures carried out by a trained technician, and thus may be impractical for use in a clinical setting.

SUMMARY

Multi-directional microfluidic devices and methods for using the same are provided. Aspects of the present disclosure include microfluidic devices that include a chamber having a separation medium, a first binding medium, and a second binding medium. In addition, the devices include a flow field element configured to subject the chamber to two or more directionally distinct flow fields. Methods of the using the devices, as well as systems and kits that include the devices are also provided. The devices, systems and methods find use in a variety of different applications, including diagnostic, research and validation assays.

BRIEF DESCRIPTION OF THE FIGURES

FIG. 1(a) shows a schematic of a microchannel and microchamber network design with fluid reservoirs numbered 1-8. FIG. 1(a), inset, shows a brightfield image of a chamber showing photopatterned gel regions: Large pore-size loading gel, PAGE separation region, Ab1 and Ab2 indicate discrete blotting regions. FIG. 1(b) shows a schematic of a multi-analyte blotting protocol according to embodiments of the present disclosure. Step 1: PAGE separation resolves proteins along the separation axis, current flow indicated by "i". Step 2: Lateral electrophoretic transfer of resolved proteins to and through the blotting regions. Step 3: Proteins bound to immobilized antibodies in each blotting region are retained, while all other species migrate out of the chamber.

FIG. 3(a) shows a graph of band distribution as a function of lateral field strength, experimental results vs. simulation. FIG. 3(b) shows a graph showing that for a given chip geometry (blotting region width and binding site density), target capture efficiency varied as a function of Da.

FIG. 5(a) shows an illustration of on-chip technique for resolution and detection of an unlabeled sample. FIG. 5(b) and FIG. 5(c) shows that the AF488 green labeled immobilized protein target was visible under green fluorescence excitation; it was initially invisible at the red wavelength until it was incubated with Texas Red (TR) labeled primary antibody.

DETAILED DESCRIPTION

Figure 1:
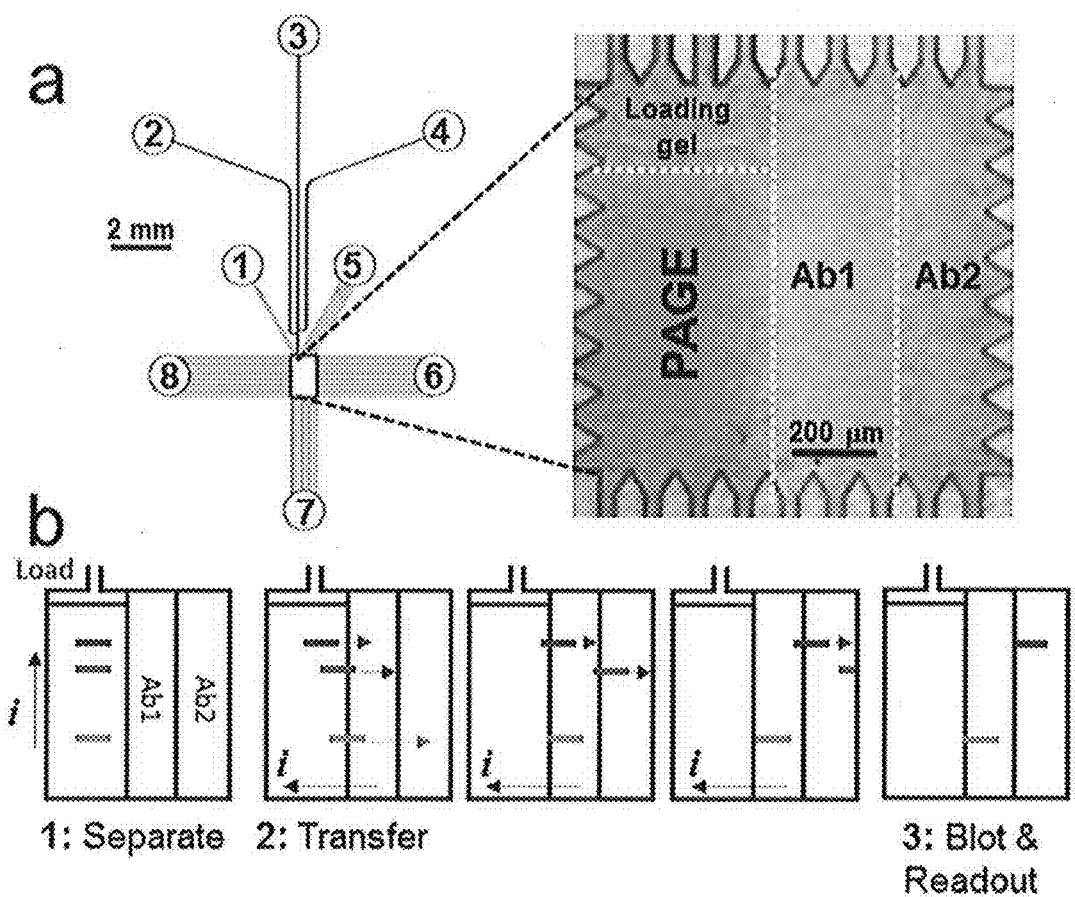
FIG. 1 shows a schematic of a microfluidic device configured for multiplexed native protein blotting according to embodiments of the present disclosure.

Multi-directional microfluidic devices and methods for using the same are provided. Aspects of the present disclosure include microfluidic devices that include a chamber having a separation medium, a first binding medium, and a second binding medium. In addition, the devices include a flow field element configured to subject the chamber to two or more directionally distinct flow fields. Methods of the using the devices, as well as systems and kits that include the devices are also provided. The devices, systems and methods find use in a variety of different applications, including diagnostic, research and validation assays.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Embodiments of the present disclosure include multi-directional microfluidic devices. By "multi-directional" is meant more than one direction, such as two or more directions, three or more directions, four or more directions, etc. In certain embodiments, two or more directions are included in a single plane, such that the two or more directions are co-planar. In some instances, the two or more directions are not co-planar, such that two directions are included in different, intersecting planes. In these cases, the two or more directions may be multi-dimensional. By "multi-dimensional" is meant more than one dimension, such as two-dimensional, three-dimensional, and the like. Directions that are multi-dimensional may occupy a region of three-dimensional space. For example, two directions that are not co-planar may each be included in different, intersecting planes, such that the intersecting planes that include the two directions occupy a region of three-dimensional space.

In certain embodiments, the microfluidic devices are configured to direct a fluid in more than one direction (e.g., the microfluidic devices are multi-directional), such as two or more directions, three or more directions, four or more directions, etc. For example, the microfluidic devices may be configured to direct a fluid in two directions, three directions, four directions, etc. In some instances, the microfluidic devices are multi-dimensional. For example, the microfluidic devices may be configured to direct a fluid in two or more directions, where the two or more directions are not co-planar, such that the two or more directions are included in two or more different, intersecting planes. In these cases, the intersecting planes that include the two or more directions may occupy a region of three-dimensional space. For instance, the microfluidic devices may be included in a substrate, such that the microfluidic device is planar. The microfluidic device may be configured to direct fluids in multiple directions within that plane. In certain embodiments, the microfluidic devices are configured to direct a fluid in multiple dimensions, such as three dimensions. For example, the microfluidic device may be configured to direct a fluid in multiple directions within the same plane, as well as direct a fluid in non-coplanar directions, such that the microfluidic device is configured to be a three-dimensional microfluidic device.

In certain embodiments, the microfluidic devices include a separation medium. The separation medium may be configured to separate the analytes in a sample from each other. In some cases, the separation medium is configured to separate the analytes in a sample based on the physical properties of the analytes. For example, the separation medium may be configured to separate the analytes in the sample based on the molecular weight, size, charge (e.g., charge to mass ratio), isoelectric point, etc. of the analytes. In certain instances, the separation medium is configured to separate the analytes in the sample based on the molecular weight of the analytes. In some cases, the separation medium is configured to separate the analytes in the sample based on the isoelectric point of the analytes (e.g., isoelectric point focusing). The separation medium may be configured to separate the analytes in the sample into distinct detectable bands of analytes. By "band" is meant a distinct detectable region where the concentration of an analyte is significantly higher than the surrounding regions. Each band of analyte may include a single analyte or several analytes, where each analyte in a single band of analytes has substantially similar physical properties, as described above.

In certain embodiments, the separation medium is configured to separate the analytes in a sample as the sample traverses the separation medium. In some cases, the separation medium is configured to separate the analytes in the sample as the sample flows through the separation medium. Aspects of the separation medium include that the separation medium has a flow path with a directional axis. By "flow path" is meant the direction a fluid sample travels as it moves. In some instances, the flow path is the direction the sample travels as the sample traverses a medium, such as a separation medium, a binding medium, and the like. As indicated above, the separation medium may have a flow path with a directional axis. In some embodiments, the directional axis of the separation flow path is aligned with the length of the separation medium. In these embodiments, the sample traverses the separation medium in the direction of the separation flow path of the separation medium (e.g., the sample may traverse the separation medium along the length of the separation medium). In some cases, the length of the separation medium is greater than the width of the separation medium, such as 2 times, 3 times, 4 times, 5 times, 10 times, 20 times, 50 times, 100 times, etc. the width of the separation medium. In some instances, the separation flow path of the separation medium is defined by a channel, such as a microfluidic channel. The separation medium may be included in a microfluidic channel, such that a sample traverses the separation medium as the sample flows through the microfluidic channel.

In certain embodiments, the separation medium includes a polymer, such as a polymeric gel. The polymeric gel may be a gel suitable for gel electrophoresis. The polymeric gel may include, but is not limited to, a polyacrylamide gel, an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular weight differences of 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content of ranging from 1% to 20%, such as from 3% to 15%, including from 5% to 10%.

In some instances, the microfluidic devices include a concentration medium positioned upstream from the separation medium. By "upstream" is meant positioned proximal to a source of a fluid flow. The concentration medium may be configured to concentrate the sample prior to the sample contacting the separation medium. The concentration medium may include a polymeric gel, such as a polymeric gel with a small pore size. For example, the concentration medium may include a polyacrylamide gel that has a total acrylamide content of ranging from 5% to 10%, such as from 5% to 9%, including from 5% to 8%, or from 5% to 7%. In some instances, the concentration medium has a total polyacrylamide content of 6%. In certain embodiments, the concentration medium includes a membrane, such as a size exclusion membrane. The small pore size of the concentration medium may slow the electrophoretic movement of the sample through the concentration medium, thus concentrating the sample before it contacts the separation medium. In some instances, the concentration membrane is configured to increase the concentration of the sample by 2 times or more, 4 times or more, 10 times or more, 25 times or more, 50 times or more, 100 times or more, 500 times or more, 1000 times or more, 2500 times or more, etc.

In certain embodiments, the subject microfluidic devices include a binding medium positioned downstream from the separation medium. By "downstream" is meant positioned distal to a source of a fluid flow. For example, the fluid flow may contact and flow through the separation medium first, followed by the binding medium. The binding medium may have a labeling flow path with a directional axis. In some instances, the labeling flow path is the direction the sample travels as the sample or analyte traverses the binding medium. The sample or analyte may traverse the binding medium in the direction of the labeling flow path of the binding medium (e.g., the sample may traverse the separation medium along the directional axis of the binding medium). The binding medium may have a directional axis the same as, or different from the directional axis of the separation medium. For example, the separation medium may have a first directional axis and the binding medium may have a second directional axis. The first directional axis may be aligned in the same direction as the second directional axis. In some cases, the first directional axis is aligned in a different direction as the second directional axis. In cases where the first directional axis is aligned in a different direction as the second directional axis, the microfluidic devices are multi-dimensional (e.g., multi-directional) microfluidic devices, as described above. For example, the second directional axis may be at an angle of 180 degrees or less with respect to the first directional axis, such as 150 degrees of less, 135 degrees or less, including 120 degrees or less, 90 degrees or less, 60 degrees or less, 45 degrees or less, or 30 degrees or less with respect to the first directional axis. In certain embodiments, the second directional axis is orthogonal to the first directional axis.

In certain cases, the binding medium includes a polymer, such as a polymeric gel or polymeric monolith. By monolith is meant a single, contiguous structure. Monoliths may include a single region with the same physical and chemical composition, or may include two or more regions that differ in terms of their physical and chemical compositions. The polymeric gel may be a gel suitable for gel electrophoresis. The polymeric gel may include, but is not limited to, a polyacrylamide gel, an agarose gel, and the like. In some cases, the binding medium may include a polyacrylamide gel that has a total acrylamide content of ranging from 1% to 20%, such as from 3% to 15%, including from 5% to 10%.

The polymeric monolith may be a monolith suitable for chromatography. The polymeric monolith may include, but is not limited to, acrylate polymers, alkylacrylate polymers, alkyl alkylacrylate polymers, copolymers thereof, and the like. In some instances, the binding medium includes a membrane. The membrane may include a nitrocellulose membrane, a polymer membrane, and the like. In some instances, the binding medium includes beads. The beads may include nitrocellulose beads, polymeric beads, combinations thereof, and the like.

In certain embodiments, the binding medium may be configured to bind to and retain an analyte of interest. In some instances, an analyte bound to the binding medium facilitates detection of the analyte. For example, the binding medium may include a binding member stably associated with a support. By "stably associated" is meant that a moiety is bound to or otherwise associated with another moiety or structure under standard conditions. In certain instances, the support is a polymeric gel or a membrane, as described above. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the binding member may be covalently bound to the support, such as cross-linked or copolymerized to the support. Covalent bonds between the binding member and the support include covalent bonds that involve reactive groups, such as, but not limited to, the following: glutaraldehyde, which utilizes the bifunctional linker glutaraldehyde to form covalent bonds with the amino/amide groups of both the binding member and the support; glycidyl methacrylate, which utilizes the glycidyl functional group (i.e., the epoxy functional group) for covalent bonding to the binding member and the methacrylate group for binding to the support; 4-nitrophenyl methacrylate, which can be used to acylate amine groups of the binding member to covalently bind to the support; N-hydroxysuccinimidyl acrylate (NHS-acrylate), which utilizes the N-hydroxysuccinimidyl group to interact with amino groups on the binding member for incorporation into the support.

A binding member can be any molecule that specifically binds to a target analyte of interest, e.g., a protein or nucleic acid sequence or biomacromolecule that is being targeted (e.g., the analyte of interest). In some embodiments, the affinity between a binding member and its target analyte to which it specifically binds when they are specifically bound to each other in a binding complex is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-18}$ M or less. "Affinity" refers to the strength of binding, increased binding affinity being correlated with a lower Kd.

Depending on the nature of the analyte, binding members can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin;

digoxin/antidigoxin; a member of a DNA or RNA aptamer binding pair; a member of a peptide aptamer binding pair; and the like.

In certain embodiments, the binding member includes an antibody. The binding member antibody may specifically bind to an analyte of interest. In some cases, the binding member is stably associated with a support, as described above. The support-bound binding member may be configured to specifically bind to the analyte of interest. As such, specific binding of the analyte of interest to the support-bound binding member may indirectly bind the analyte of interest to the support. Binding of the analyte of interest to the support may stably associate the analyte with the support and thus facilitate detection of the analyte of interest.

In certain embodiments, two or more different binding members are stably associated with the binding medium. The two or more different binding members may specifically bind to the same or different analytes. In some cases, the two or more different binding members may specifically bind to the same analyte. For instance, the two or more different binding members may include different antibodies specific for different epitopes on the same analyte. In other cases, the two or more different binding members may specifically bind to different analytes. For example, the two or more binding members may include different antibodies specific for epitopes on different analytes.

In certain embodiments, the microfluidic device includes one or more binding media, such as two or more binding media. For instance, the microfluidic device may include a first binding medium and a second binding medium. Each binding medium may have the same composition, or in other embodiments may have different compositions. For example, the first binding medium may have a first binding member stably associated with the first binding medium, and the second binding medium may have a second binding member stably associated with the second binding medium. In some cases, the first and second binding members may specifically bind to different analytes. In other instances, the first and second binding members may specifically bind to different epitopes of the same analyte. In embodiments, where the first and second binding members specifically bind to different analytes, the microfluidic device may be configured to detect the presence of two or more analytes in a sample, where a first analyte is specifically bound by the first binding member of the first binding medium and a second analyte is specifically bound by the second binding member of the second binding medium. The microfluidic device may include more than two binding media, each configured to specifically bind to different analytes in the sample, such that the microfluidic device is configured to detect multiple different analytes in the sample. For instance, the microfluidic device may include 2 or more, or 3 or more, or 4 or more, or 5 or more, or 6 or more, or 7 or more, or 8 or more, or 9 or more, or 10 or more binding mediums.

In certain embodiments, the microfluidic device is configured to contact the first binding medium before contacting the second binding medium. For example, the first binding medium may be positioned between the separation medium and the second binding medium. Additional binding media may be provided in series following the second binding medium. In certain cases, the binding media have the same directional axis, such that a sample flows from the first binding medium to the second binding medium along the same directional axis. As described above, the directional axis of the binding media may be at an angle to the directional axis of the separation medium, such as orthogonal to the directional axis of the separation medium.

Aspects of the microfluidic devices include embodiments where the separation medium is in fluid communication with the binding medium. In certain embodiments, the binding medium is arranged downstream from the separation medium. The microfluidic device may be configured to direct the sample through the separation medium first to produce a separated sample. In certain embodiments, the microfluidic device is configured such that the separation medium and the binding medium are in direct fluid communication with each other. For example, the separation medium may be in direct contact with the binding medium. In some cases, the separation medium and the binding medium are bound to each other, such as co-polymerized. Embodiments where the separation medium is in direct fluid communication with the binding medium may facilitate the transfer of moieties from the separation medium to the binding medium or transfer of moieties from the binding medium to the separation medium with a minimal loss of moieties. In some instances, the microfluidic devices are configured such that moieties are quantitatively transferred from one medium to another (e.g., from the separation medium to the binding medium, or from the binding medium to the separation medium).

In certain embodiments, the microfluidic device is configured to direct the separated sample through the binding medium. In some instances, the microfluidic devices are configured such that the sample or analyte traverses from the separation medium to an intervening channel or medium and then traverses to the binding medium. In other cases, the microfluidic device is configured such that the separation medium and the binding medium are in direct fluid communication with each other, such that a sample or analyte can traverse directly from the separation medium to the binding medium. As described above, the binding medium may include binding members configured to bind to an analyte for detection of an analyte of interest in the separated sample.

In some instances, the microfluidic device is configured to subject a sample to two or more directionally distinct flow fields. By "flow field" is meant a region where moieties traverse the region in substantially the same direction. For example, a flow field may include a region where mobile moieties move through a medium in substantially the same direction. A flow field may include a medium, such as a separation medium, a binding medium, a loading medium, etc., where moieties, such as buffers, analytes, reagents, etc., move through the medium in substantially the same direction. A flow field may be induced by an applied electric field, a pressure differential, electroosmosis, and the like. In some embodiments, the two or more flow fields may be directionally distinct. For example, a first flow field may be aligned with the directional axis of the separation flow path of the separation medium. The first flow field may be configured to direct the sample or analytes through the separation medium along the separation flow path. A second flow field may be aligned with the directional axis of the labeling flow path of the binding medium. In some instances, the second flow field is configured to direct the sample or analytes through the binding medium along the labeling flow path. The second flow field may be configured to direct the sample or analytes through the binding medium such that the analyte of interest contacts its specific binding member. In some instances, the second flow field is configured to direct a binding member through the binding medium along the labeling flow path. The second flow field may be configured to direct the binding member through the binding medium such that the binding member contacts its specific analyte of interest. As described above, in certain instances, the directional axis of the labeling flow path is orthogonal to the directional axis of the separation flow path. In these instances, the second flow field may be orthogonal to the first flow field.

In certain embodiments, the microfluidic device is configured to subject a sample to two or more directionally distinct electric fields. The electric fields may facilitate the movement of the sample through the microfluidic device (e.g., electrokinetic transfer of the sample from one region of the microfluidic device to another region of the microfluidic device). The electric fields may also facilitate the separation of the analytes in the sample by electrophoresis (e.g., polyacrylamide gel electrophoresis (PAGE)), as described above. For instance, the electric field may be configured to direct the analytes in a sample through the separation medium of the microfluidic device. The electric field may be configured to facilitate the separation of the analytes in a sample based on the physical properties of the analytes. For example, the electric field may be configured to facilitate the separation of the analytes in the sample based on the molecular weight, size, charge (e.g., charge to mass ratio), isoelectric point, etc. of the analytes. In certain instances, the electric field is configured to facilitate the separation of the analytes in the sample based on the molecular weight of the analytes. In some cases, the electric field is configured to facilitate the separation of the analytes in the sample based on the isoelectric point of the analytes.

In some embodiments, the two or more electric fields may be directionally distinct. For example, a first electric field may be aligned with the directional axis of the separation flow path of the separation medium. The first electric field may be configured to direct the sample or analytes through the separation medium along the separation flow path. A second electric field may be aligned with the directional axis of the labeling flow path of the binding medium. In some instances, the second electric field is configured to direct the sample or analytes through the binding medium (e.g., the two or more binding media, such as the first binding medium and the second binding medium) along the labeling flow path. The second electric field may be configured to direct the sample or analytes through the first binding medium and the second binding medium such that the analyte(s) of interest contacts its specific binding member in the first and/or second binding media.

In some instances, the second electric field is configured to direct a binding member through the binding medium along the labeling flow path. The second electric field may be configured to direct the binding member through the binding medium such that the binding member contacts its specific analyte of interest. As described above, in certain instances, the directional axis of the labeling flow path is orthogonal to the directional axis of the separation flow path. In these instances, the second electric field may be orthogonal to the first electric field. In some cases, two or more binding members may be directed through the binding media (e.g., the first binding medium and the second binding medium) along the labeling flow path such that the binding members (e.g., the first binding member and the second binding member) contact their respective analytes of interest.

In certain embodiments, the microfluidic device includes one or more electric field generators configured to generate an electric field. The electric field generator may be configured to apply an electric field to various regions of the microfluidic device, such as one ore more of the separation medium, the binding medium, the loading medium, and the like. The electric field generators may be configured to electrokinetically transport the analytes and moieties in a sample through the various media in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below.

The microfluidic devices may include one or more channels that include a separation medium and first and second binding media, as described above. The microfluidic devices may include a binding channel that includes a binding medium, as described above. In some instances, the separation channel is in fluid communication with the binding channel, such that the separation medium in the separation channel is in fluid communication with the binding medium in the binding channel. Some embodiments of the microfluidic devices include a separation channel and a binding channel, where the separation channel has a first directional axis and the binding channel has a second directional axis. The first directional axis and the second directional axis may be aligned in the same direction as each other or may be aligned in different directions from each other. For example, the directional axis of the separation channel may be at an angle of 180 degrees or less with respect to the binding channel, such as 150 degrees of less, 135 degrees or less, including 120 degrees or less, 90 degrees or less, 60 degrees or less, 45 degrees or less, or 30 degrees or less with respect to the binding channel. In certain embodiments, the directional axis of the binding channel is orthogonal to the directional axis of the separation channel.

Embodiments of the microfluidic channels may be made of any suitable material that is compatible with the microfluidic devices and compatible with the samples, buffers, reagents, etc. used in the microfluidic devices. In some cases, the microfluidic channels are made of a material that is inert (e.g., does not degrade or react) with respect to the samples, buffers, reagents, etc. used in the subject microfluidic devices and methods. For instance, the microfluidic channels may be made of materials, such as, but not limited to, glass, quartz, polymers, elastomers, paper, combinations thereof, and the like.

In certain embodiments, the microfluidic channels have a width ranging from 1 µm to 500 µm, such as from 5 µm to 300 µm, including from 10 µm to 200 µm, for example from 50 µm to 150 µm. In some instances, the microfluidic channels have a width of 100 µm. In certain embodiments, the microfluidic channels have a depth ranging from 1 µm to 200 µm, such as from 5 µm to 100 µm, including from 10 µm to 50 µm. In some cases, the microfluidic channels have a depth of 25 µm.

In some instances, the microfluidic devices include one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In some aspects, the separation and binding media are provided in a single common chamber. In these embodiments, the microfluidic devices include a chamber. The chamber may include a separation medium and a binding medium. As described above, the separation medium may be in fluid communication, such as in direct physical contact, with the binding medium. In some cases, the separation medium is bound to the binding medium, such as copolymerized or cross-linked to the binding medium. As such, the chamber may be configured to contain both the separation medium and the binding medium in fluid communication with each other. The chamber may be configured to contain the separation medium and the binding medium such that the separation flow path of the separation medium is upstream from the labeling flow path of the binding medium.

In addition to the separation medium and the binding medium, the chamber may also include a loading medium. The loading medium may be in fluid communication with the separation medium. In some instances, the loading medium is in direct physical contact with the separation medium. For example, the loading medium may be bound to the separation medium, such as cross-linked or copolymerized with the separation medium. The loading medium may be positioned upstream from the separation medium, such that the sample contacts the loading medium before contacting the separation medium. In certain embodiments, the loading medium facilitates contacting a sample with the separation medium. For instance, the loading medium may be configured to concentrate the sample before the sample contacts the separation medium. In certain embodiments, the loading medium may include two or more regions that have different physical and/or chemical properties. For example, the loading medium may include a loading region and a stacking region. The loading medium may be configured to include a loading region upstream from a stacking region.

In certain embodiments, the loading medium includes a polymer, such as a polymeric gel. The polymeric gel may be a gel suitable for gel electrophoresis. The polymeric gel may include, but is not limited to, a polyacrylamide gel, an agarose gel, and the like. In some cases, the loading region includes a polymeric gel with a large pore size. For example, the loading region may include a polyacrylamide gel that has a total acrylamide content of 5% or less, such as 4% or less, including 3% or less, or 2% or less. In some instances, the loading region has a total polyacrylamide content of 3%. In some cases, the stacking region of the loading medium may be configured to concentrate the sample before the sample contacts the separation medium. The stacking region may include a polymeric gel with a small pore size (e.g., the stacking region may have a pore size smaller than the pore size of the loading region). For example, the stacking region may include a polyacrylamide gel that has a total acrylamide content of ranging from 5% to 10%, such as from 5% to 9%, including from 5% to 8%, or from 5% to 7%. For instance, the stacking region may have a total polyacrylamide content greater than that of the loading region. In some instances, the stacking region has a total polyacrylamide content of 6%. The small pore size of the stacking region may slow the electrophoretic movement of the sample through the stacking region, thus concentrating the sample before it contacts the separation medium.

In certain instances, the chamber contains the loading medium, the separation medium and the binding medium. The chamber may be configured to contain the loading medium, the separation medium and the binding medium such that the loading medium, the separation medium and the binding medium are in fluid communication with each other, as described above. For example, the chamber may include a contiguous polymeric gel with various regions. Each region of the contiguous polymeric gel may have different physical and/or chemical properties. The contiguous polymeric gel may include a first region having a loading medium, a second region having a separation medium and a third region having a binding medium. The flow paths of each region of the polymeric gel may be configured such that a sample first contacts the loading medium, then contacts the separation medium, and finally contacts the binding medium.

In certain embodiments, the polymeric gel has a width ranging from 0.1 mm to 5 mm, such as from 0.2 mm to 2.5 mm, including from 0.5 mm to 1.5 mm. In some cases, the polymeric gel has a width of 1.0 mm. In some instances, the polymeric gel has a length ranging from 0.5 mm to 5 mm, such as from 0.5 mm to 3 mm, including from 1 mm to 2 mm. In certain instances, the polymeric gel has a length of 1.5 mm. In certain embodiments, the first region of the polymeric gel that includes the loading medium has a width ranging from 0.1 mm to 5 mm, such as from 0.2 mm to 2.5 mm, including from 0.5 mm to 1.5 mm. In some cases, the first region of the polymeric gel that includes the loading medium has a width of 0.9 mm. In some cases, the first region of the polymeric gel that includes the loading medium has a length ranging from 0.1 mm to 2 mm, such as from 0.1 mm to 1 mm, including from 0.1 mm to 0.5 mm. In certain embodiments, the first region of the polymeric gel that includes the loading medium has a length of 0.2 mm. In certain instances, the second region of the polymeric gel that includes the separation medium has a width ranging from 0.1 mm to 5 mm, such as from 0.2 mm to 2.5 mm, including from 0.5 mm to 1.5 mm. In some cases, the second region of the polymeric gel that includes the separation medium has a width of 0.9 mm. In some cases, the second region of the polymeric gel that includes the separation medium has a length ranging from 0.5 mm to 5 mm, such as from 0.5 mm to 3 mm, including from 1 mm to 2 mm. In certain embodiments, the second region of the polymeric gel that includes the separation medium has a length of 1.3 mm. In certain instances, the third region of the polymeric gel that includes the binding medium has a width ranging from 0.01 mm to 2 mm, such as from 0.01 mm to 1 mm, including from 0.05 mm to 0.5 mm. In some cases, the third region of the polymeric gel that includes the bonding medium has a width of 0.1 mm. In some cases, the third region of the polymeric gel that includes the binding medium has a length ranging from 0.5 mm to 5 mm, such as from 0.5 mm to 3 mm, including from 1 mm to 2 mm. In certain embodiments, the third region of the polymeric gel that includes the binding medium has a length of 1.5 mm.

In certain embodiments, the microfluidic device has a width ranging from 10 cm to 1 mm, such as from 5 cm to 5 mm, including from 1 cm to 5 mm. In some instances, the microfluidic has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

In certain embodiments, the microfluidic device is substantially transparent. By "transparent" is meant that a substance allows visible light to pass through the substance.

In some embodiments, a transparent microfluidic device facilitates detection of analytes bound to the binding medium, for example analytes that include a detectable label, such as a fluorescent label. In some cases, the microfluidic device is substantially opaque. By "opaque" is meant that a substance does not allow visible light to pass through the substance. In certain instances, an opaque microfluidic device may facilitate the analysis of analytes that are sensitive to light, such as analytes that react or degrade in the presence of light.

Methods

Embodiments of the methods are directed to determining whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a numerical measurement of the concentration of the analyte is provided to the user.

In certain embodiments, the microfluidic devices are configured to detect the presence of one or more analytes in a sample. Samples that may be assayed with the subject microfluidic devices may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular weight, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In some embodiments, the analyte of interest can be identified so that the presence of the analyte of interest can then be detected. For instance, the method may include evaluating the binding medium (e.g., the first and second binding media) for the presence of two or more analytes. Analytes may be identified by any of the methods described herein. For example, a labeling agent, such as an analyte specific binding member that includes a detectable label may be employed. Detectable labels include, but are not limited to, fluorescent labels, colorimetric labels, chemiluminescent labels, enzyme-linked reagents, multicolor reagents, avidin-streptavidin associated detection reagents, non-visible detectable labels (e.g., radiolabels, gold particles, magnetic labels, electrical readouts, density signals, etc.), and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2' disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7' dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla* mulleri, or *Ptilosarcus guernyi*; "humanized" recombinant GFP (hrGFP); any of a variety of fluorescent and colored proteins from *Anthozoan* species; combinations thereof; and the like.

In certain embodiments, the method includes introducing a fluid sample into a microfluidic device. Introducing the fluid sample into the microfluidic device may include directing the sample through a separation medium to produce a separated sample. In some cases, the separated sample is produced by gel electrophoresis as the sample traverses the separation medium, as described above. The separated sample may include distinct detectable bands of analytes, where each band includes one or more analytes that have substantially similar properties, such as molecular weight, size, charge (e.g., charge to mass ratio), isoelectric point, etc. depending on the type of gel electrophoresis performed.

Aspects of the methods may also include transferring the separated sample to a binding medium (e.g., a first binding medium and a second binding medium). In certain embodiments, the method includes directing the separated sample through the binding media (e.g., the first and second binding mediums). In other embodiments, specific bands of analytes in the separated sample may be selectively transferred to the binding media. In some cases, the method includes contacting an analyte or analytes of interest with a binding member in the binding medium. The binding member may specifically bind to the analyte, thus retaining the analyte in the binding medium. Moieties not of interest are not specifically bound by the binding members in the binding medium. For example, the microfluidic device may include a first binding medium and a second binding medium as described above.

In these embodiments, the method may include contacting a first analyte of interest with a first binding member in the first binding medium and contacting a second analyte of interest with a second binding member in the second binding medium.

In certain embodiments, the method includes evaluating the binding medium (e.g., the first and second binding mediums) for the presence of the analyte or analytes of interest (e.g., the two or more analytes of interest). For example, in some cases, the method includes detecting the analyte(s) bound to the binding media. Detectable binding of an analyte of interest to the binding members in the binding media indicates the presence of the analyte or analytes of interest in the sample. Moieties not of interest that traverse the binding media and do not bind to the binding members in the binding media may be washed away or transferred to a secondary analysis device such as, but is not limited to, a UV spectrometer, and IR spectrometer, a mass spectrometer, an HPLC, an affinity assay device, and the like.

In certain embodiments, the method includes transferring a binding member (e.g., a labeling agent, as described above) to the separated sample. Binding members may be transferred from the binding medium to specific bands of analytes in the separated sample. In some instances, the method includes contacting the binding member with an analyte of interest in the separated sample. In some cases, method includes stably associating the separated sample with the separation medium. For example, the method may include binding the separated sample to the separation medium. The separated sample may be chemically or physically bound to the separation medium, such as by contacting the separated sample with chemical reagents, cross-linking the separated sample to the separation medium, and the like. The binding member may specifically bind to an analyte or interest, thus retaining the binding member in the separation medium where the bound binding members may be subsequently detected. Binding members that do not specifically bind to analytes in the separated sample may be transferred through the separation medium.

In certain embodiments, the separated sample is contacted with the binding media as described above, for instance by flowing the separated sample from the separation medium to the binding media. As described above, the binding media may include one or more binding members stably associated with the binding media, such that the analyte or analytes of interest are specifically bound by the binding members to the binding media. In certain cases, detecting the analyte or analytes of interest includes flowing a labeling agent through the binding medium. The labeling agent may be an analyte specific binding member that includes a detectable label, as described above. The labeling agent may specifically bind to and thus label the specific analyte of interest. In some cases, two or more labeling agents may be used, for instance a first labeling agent and a second labeling agent may be flowed through the first and second binding media and may specifically bind to a first analyte of interest and a second analyte of interest. The first and second binding media may be evaluated for the presence of the two or more analytes.

In some cases, false-positive signals due to non-specific binding of the binding member to moieties not of interest are minimized. For example, non-specific binding of the binding member to other moieties not of interest may be minimized and the moieties not of interest will not be detected. The moieties not of interest may traverse through the binding medium without binding to the binding member. Thus, the binding member may specifically bind only to the analyte of interest. Specific binding of the binding member to only the analyte of interest may facilitate the specific detection of the analyte of interest in complex samples.

In certain embodiments, the method includes concentrating, diluting, or buffer exchanging the sample prior to directing the sample through the separation medium. Concentrating the sample may include contacting the sample with a concentration medium prior to contacting the sample with the separation medium. As described above, the concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes transferring moieties that are not bound by the binding members in the binding medium away from the binding medium. The unbound moieties may be directed to a transfer flow path that is in fluid communication with the labeling flow path of the binding medium. In some cases, the method includes transferring the unbound moieties to a waste reservoir. In other cases, the method includes directing the unbound moieties downstream from the binding medium for secondary analysis with a secondary analysis device such as, but is not limited to, a UV spectrometer, and IR spectrometer, a mass spectrometer, an HPLC, an affinity assay device, and the like.

Embodiments of the method may also include releasing the analyte bound to the binding medium. The releasing may include contacting the bound analyte with a releasing agent. The releasing agent may be configured to disrupt the binding interaction between the analyte and the binding member. In some cases, the releasing agent is a reagent, buffer, or the like, that disrupts the binding interaction between the analyte and the binding member causing the binding member to release the analyte. After releasing the analyte from the binding member, the method may include transferring the analyte away from the binding medium. For example, the method may include directing the released analyte downstream from the binding medium for secondary analysis with a secondary analysis device such as, but is not limited to, a UV spectrometer, and IR spectrometer, a mass spectrometer, an HPLC, an affinity assay device, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular weight, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

In certain embodiments, the method is an automated method. As such, the method may include a minimum of user interaction with the microfluidic devices and systems after introducing the sample into the microfluidic device. For example, the steps of directing the sample through the separation medium to produce a separated sample and transferring the separated sample to the binding medium may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

Systems

Aspects of certain embodiments include a system for detecting an analyte in a sample. In some instances, the system includes a microfluidic device as described herein. The system may also include a detector. In some cases, the detector is a detector configured to detect a detectable label. As described above, the detectable label may be a fluorescent label. For example, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector to determine the presence of the analyte bound to the binding member.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, sample solutions, buffers (e.g., release buffers, wash buffers, electrophoresis buffers, etc.), and the like. In certain embodiments, the microfluidic fluid handling components are configured to deliver a fluid to the separation medium of the microfluidic device, such that the fluid contacts the separation medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 μL or less, including 100 μL or less, for example 50 μL or less, or 25 μL or less, or 10 μL or less, or 5 μL or less, or 1 μL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation flow path of the separation medium. As such, the applied electric field may be configured to electrokinetically transport the analytes and moieties in a sample through the separation medium. In certain embodiments, the system includes an electric field generator configured to apply an electric field such that analytes and/or moieties in the sample are electrokinetically transported from the separation medium to the binding medium. For instance, an applied electric field may be aligned with the directional axis of the labeling flow path of the binding medium. In some cases, the applied electric field is configured to electrokinetically transport selected analytes that have been separated by the separation medium. Selected analytes that have been separated by the separation medium may be transported to the binding medium by applying an appropriate electric field along the directional axis of the labeling flow path of the binding medium. In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium and/or the binding medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, 8 or more, 10 or more, 50 or more, or 100 or more microfluidic devices. In certain embodiments, the microfluidic devices can be arranged into an array with an area of less than 10 cm$^2$, or less than 5 cm$^2$, e.g., less than 1 cm$^2$, including less than 50 mm$^2$, less than 20 mm$^2$, such as less than 10 mm$^2$, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 μL or less, such as 75 μL or less, including 50 μL or less, or 25 μL or less, or 10 μL or less, for example, 5 μL or less, 2 μL or less, or 1 μL or less while still producing detectable results. In certain embodiments, the system is configured to have a detection sensitivity of 10 nM or less, or 5 nM or less, or 1 nM or less, such as 500 pM or less, including 100 pM or less, or 50 pM or less, for instance, or 10 pM or less, or 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 μg/mL or less, such as 500 ng/mL or less, including 100 ng/mL or less, for example, 10 mg/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-8}$ M.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

The subject devices, systems and methods find use in a variety of different applications where determination of the presence or absence, and/or quantification of one or more analytes in a sample is desired. In certain embodiments, the methods are directed to the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern, Far-Western blotting, Southwestern blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods finds use in portable and point-of-care or near-patient molecular diagnostics.

In certain embodiments, the subject devices, systems and methods find use in detecting biomarkers for a disease or disease state. In some cases, the disease is a cellular proliferative disease, such as but not limited to, a cancer, a tumor, a papilloma, a sarcoma, or a carcinoma, and the like. In certain instances, the subject devices, systems and methods find use in detecting biomarkers for the characterization of cell signaling pathways and intracellular communication for drug discovery and vaccine development. For example, the subject devices, systems and methods find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include, but are not limited to the following: prostate specific antigen (PSA), which is a prostate cancer biomarker; C-reactive protein, which is an indicator of inflammation; transcription factors, such as p53, which facilitates cell cycle and apoptosis control; polyamine concentration, which is an indicator of actinic keratosis and squamous cell carcinoma; proliferating cell nuclear antigen (PCNA), which is a cell cycle related protein expressed in the nucleus of cells that are in the proliferative growth phase; growth factors, such as IGF-I; growth factor binding proteins, such as IGFBP-3; micro-RNAs, which are single-stranded RNA molecules of about 21-23 nucleotides in length that regulate gene expression; carbohydrate antigen CA19.9, which is a pancreatic and colon cancer biomarker; cyclin-dependent kinases; epithelial growth factor (EGF); vascular endothelial growth factor (VEGF); protein tyrosine kinases; over-expression of estrogen receptor (ER) and progesterone receptor (PR); and the like. For example, the subject devices, systems and methods may be used to detect and/or quantify the amount of endogenous prostate specific antigen (PSA) in diseased, healthy and benign samples.

In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like. For example, the subject devices, systems and methods may be used to monitor HIV viral load and patient CD4 count for HIV/AIDS diagnosis and/or therapy monitoring by functionalizing the sensor surface with antibodies to HIV capsid protein p24, glycoproteins 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like. For example, the subject devices, systems and methods can be used to detect gastrointestinal infections, such as but not limited to, aseptic meningitis, botulism, cholera, *E. coli* infection, hand-foot-mouth disease, *helicobacter* infection, hemorrhagic conjunctivitis, herpangina, myocaditis, paratyphoid fever, polio, shigellosis, typhoid fever, vibrio septicemia, viral diarrhea, etc. In addition, the subject devices, systems and methods can be used to detect respiratory infections, such as but not limited to, adenovirus infection, atypical pneumonia, avian influenza, swine influenza, bubonic plague, diphtheria, influenza, measles, meningococcal meningitis, mumps, parainfluenza, pertussis (i.e., whooping cough), pneumonia, pneumonic plague, respiratory syncytial virus infection, rubella, scarlet fever, septicemic plague, severe acute respiratory syndrome (SARS), tuberculosis, etc. In addition, the subject devices, systems and methods can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject devices, systems and methods can be used to detect urogenital diseases, such as but not limited to, AIDS, chancroid, Chlamydia, condyloma accuminata, genital herpes, gonorrhea, lymphogranuloma venereum, non-gonococcal urethritis, syphilis, etc. In addition, the subject devices, systems and methods can be used to detect viral hepatitis diseases, such as but not limited to, hepatitis A, hepatitis B, hepatitis C, hepatitis D, hepatitis E, etc. In addition, the subject devices, systems and methods can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject devices, systems and methods can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject devices, systems and methods can be used to detect arbovirus infections, such as but not limited to, Dengue hemorrhagic fever, Japanese encephalitis, tick-borne encephalitis, West Nile fever, Yellow fever, etc. In addition, the subject devices, systems and methods can be used to detect antibiotics-resistance infections, such as but not limited to, *Acinetobacter baumannii, Candida albicans, Enterococci* sp., *Klebsiella pneumoniae, Pseudomonas aeruginosa, Staphylococcus aureus*, etc. In addition, the subject devices, systems and methods can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc. Similarly, the subject devices, systems and methods can be used to detect cardiovascular diseases, central nervous diseases, kidney failures, diabetes, autoimmune diseases, and many other diseases.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. The kits may further include a buffer. For instance, the kit may include a buffer, such as an electrophoretic buffer, a sample buffer, and the like. The kits may further include additional reagents, such as but not limited to, release agents, denaturing agents, refolding agents, detergents, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

I. Summary

Experiments were performed to demonstrate multiplexed native Western blotting in a rapid, automated and unified microfluidic format. Assay and microdevice designs integrated protein binding (e.g., blotting) against multiple antibody binding regions with native polyacrylamide gel electrophoresis. This microfluidic integration strategy overcame non-specific material losses inherent to antibody stripping steps typically needed for conventional re-blotting techniques, which can limit analyte quantitation. To inform rational design of the multiplexed microfluidic device an analytical model was developed for analyte capture on the binding regions. Comparison to empirical observations was reported, with capture efficiencies of 85% or greater. Label free detection made simultaneous and quantitative multiplexed measurements possible without the need for pre-labeling of the sample. Assay linear dynamic range ranged from 8 nM to 800 nM with assay completion in 5 min.

II. Experimental

A. On-Chip Multi-Analyte Immunoblotting.

The multiplexed immunoblotting assay was housed in a single 1 mm×1.5 mm microchamber and microfluidic channel network (FIG. 1(a)). To fabricate the multiplexed device, the microchamber was patterned with polyacrylamide (PA) gel with specific regions for PAGE (loading and separation gels) and discrete antibody-patterned PA gel binding regions that parallel the PAGE separation axis. To load the proteins into the central chamber, a ~2 μL sample volume was first pipetted into the sample reservoir (FIG. 1(a), reservoir 2). An electric potential maintained across reservoirs 2 and 4 resulted in a ~0.5 mL sized plug of protein formed at the cross channel intersection. As depicted in FIG. 1(b), proteins were then electrophoretically injected and separated in a native PAGE region of the chamber. The separation region was comprised of a stacking interface (large-to-small pore size discontinuity, 3% T-to-6% T, w/v) and separation gel (6% T). As electrophoresis proceeded, proteins were resolved owing to differences in charge-to-mass ratio (FIG. 1(b), step 1). Control of voltages at electrodes 1 and 5 minimized sample dispersion and preserved high resolution analyte separation (see voltage program, Table 1).

TABLE 1

On-chip immunoblotting voltage control program for high voltage power supply

| | Applied Voltage/Current | | | | | | | |
|---|---|---|---|---|---|---|---|---|
| | Electrode 1 | Electrode 2 | Electrode 3 | Electrode 4 | Electrode 5 | Electrode 6 | Electrode 7 | Electrode 8 |
| 1. Sample loading | 0 μA | −400 V | −0.1 μA | −200 V | 0 μA | 0 μA | −0.05 μA | 0 μA |
| 2. Injection/separation | −290 V | 0.1 μA | −400 V | 0.1 μA | −295 V | 0 μA | −220 V | 0 μA |
| 3. Transfer & blotting | 0 μA | 0.05 μA | 0 μA | 0.05 μA | 0 μA | −50 V | 0 μA | −120 V |

The high voltage power supply was connected to 8 programmable electrodes. Each of the 8 programmable electrodes was capable of current/voltage feedback control with a dynamic range of approximately 4000V and estimated +/−0.01 μA current and 1V voltage resolution.

At separation completion, the separation electric field was removed and a lateral field was applied across the chamber, thus directing separated protein peaks to the antibody functionalized binding regions (FIG. 1(b), step 2). Each binding region included biotinylated capture antibody (specific to a protein target) linked to PA gel through a streptavidin-conjugated acrylamide. Use of this adaptable linkage chemistry allowed the blotting region to be customized with biotinylated antibodies prior to assay initiation. As an example in FIG. 1, two distinct binding regions patterned with different antibodies (Ab1, Ab2) are shown.

The microchannel arrays bordering the central chamber maintained electric field uniformity along the separation and electrotransfer axes during PAGE separation and transfer, respectively. The transfer step maintained the separation resolution (SR) from the separation axis to the binding regions. A 1:1 spatial mapping of protein position on the separation axis to position on the binding region was required to preserve charge-to-mass information. Thus, peak dispersion during electrotransfer was minimized. In FIG. 1(b), step 3, proteins with an affinity for an immobilized antibody became immobilized as an immune-complex in the relevant binding region. This in-gel binding process was performed on a time scale of minutes. Protein species with low-to-no affinity for the immobilized antibody migrated through and out channel of the binding region without being retained.

B. Reagents and Samples.

Tris-glycine (25 mM Tris, 192 mM Glycine at pH 8.3) diluted to 1× was used as the sample and run buffer (Bio-Rad Laboratories, Hercules, Calif.). PA gels were prepared from a 30% acrylamide (29:1 acrylamide/bisacrylamide ratio) stock solution (Sigma-Aldrich, St. Louis, Mo.). Antibody functionalized blotting gels were prepared from a precursor solution which also contained streptavidin acrylamide (Invitrogen, Carlsbad, Calif.). All gel precursor solutions contained 0.2% (w/v) 2,2'-Azobis-[2-methyl-N-(2-hydroxyethyl) propionamide] (VA-086) from Wako Chemicals (Richmond, Va.) as a photoinitiator.

A fluorescently labeled protein ladder consisting of C-reactive protein (CRP) at 770 nM (EMD Chemicals Inc., Darmstadt, Germany), protein G (PG) at 550 nM and trypsin inhibitor (TI) at 133 nM (Invitrogen) was utilized for device and assay characterization. CRP was labeled in-house with AlexaFluor 488 (Invitrogen) according to manufacturer's instructions while PG and TI were purchased, already labeled by the vendor. Biotinylated anti-protein G (α-PG) antibodies were obtained from Abcam (Cambridge, Mass.), and biotinylated anti-CRP (α-CRP) was purchased from R&D Systems (Minneapolis, Minn.). Alternatively, antibodies can be conjugated using commercially available biotinylation kits (Thermo Scientific, Rockford, Ill.).

C. Multi-Analyte Blotting Chip Fabrication.

Glass microfluidic chips were designed in-house with initial wet etching of glass conducted by Caliper Life Sciences (Hopkinton, Mass.). The fluid access vias were drilled (Crystalite, Lewis Center, Ohio/Cameron Microdrill Presses, Sonora, Calif.) and chips were thermally bonded (Vulcan 3-550, Neytech, York, Pa.) in-house. Prior to the introduction of gel precursor solutions, the glass chips were first incubated for 30 minutes with a 2:2:3:3 mixture of silane (3-(trimethoxysilyl) propyl methacrylate, Sigma-Aldrich), acetic acid, methanol and water. This surface silanization step was critical to eliminating shifting of gel boundaries sometimes observed with extended application of an electric field (i.e., >20 minutes) when silanization was not performed. After glass chip fabrication, three types of gels were fabricated in the 2D chamber: large pore-size loading gel (3% T, 3.3% C), smaller pore-size separation gel (6% T, 3.3% C) and antibody functionalized gel (4% T, 3.3% C containing 3.8 μM streptavidin-acrylamide) gels. Biotinylated antibodies were included at 1.6 μM in the blotting gel precursor solution and incubated for 1 hour at room temperature (25° C.) prior to PA gel photopolymerization.

Figure 6:
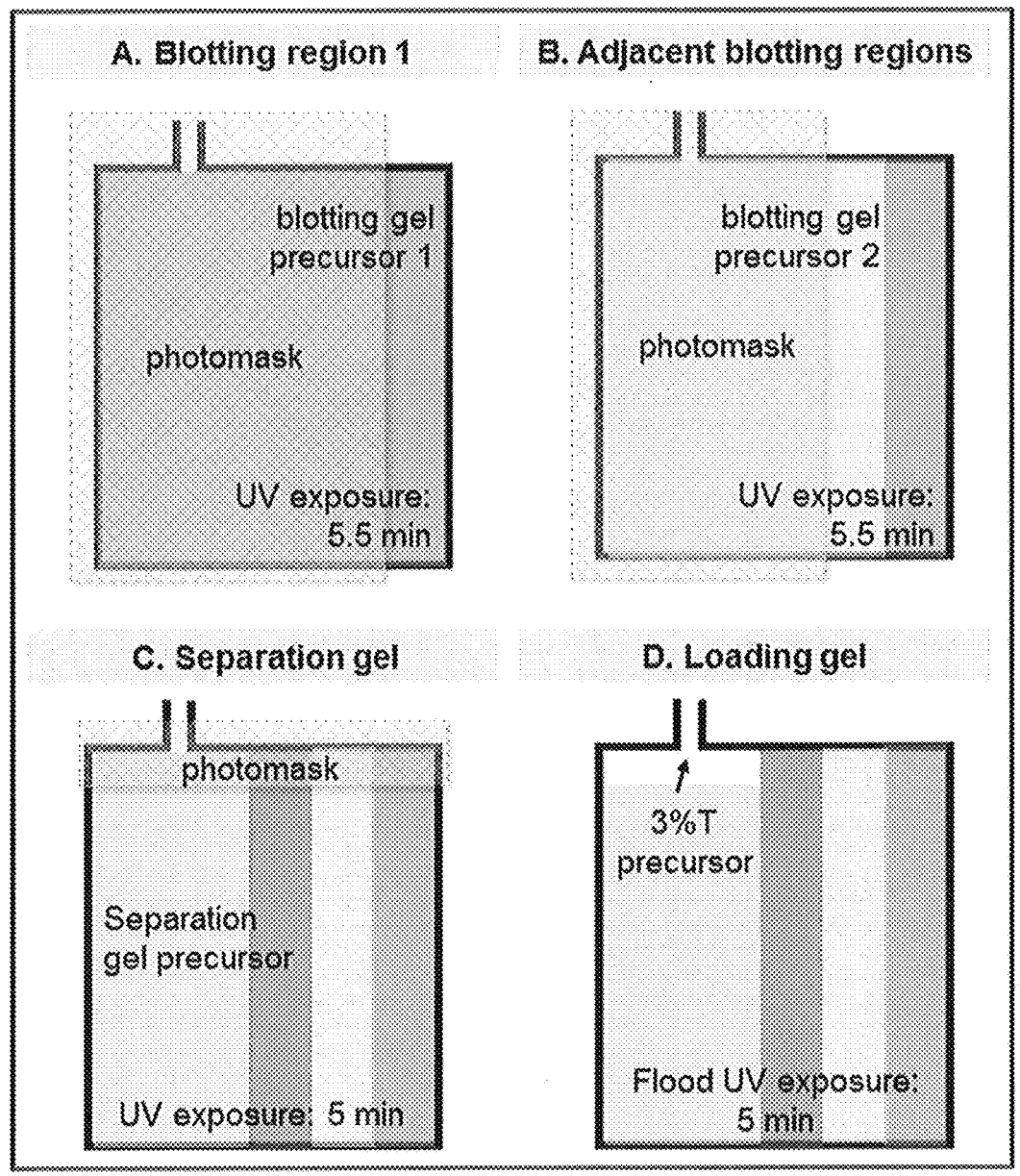
FIG. 6 shows a schematic of a multi-step photolithography process that enables fabrication of multiple PA gel regions with varying physical and functional properties according to embodiments of the present disclosure. The fabrication approach yields a device suitable for fully-automated, low sample loss, multi-analyte native Western blotting.

Integration of discrete gel zones within a single device was enabled by a multistep photolithographic process (FIG. 6). FIG. 6 shows a schematic diagram of multistep photolithographic gel fabrication. A Hamamatsu LightningCure LC5 UV light source (Hamamatsu City, Japan) with variable intensity control was used for photopatterning of the gels. The UV beam from the LC5 was directed along the light path of a Nikon Diaphot 200 (Tokyo, Japan) inverted microscope and up through a UV-transmission objective lens (UPLANS-APO 4×, Olympus, Melville, N.Y.). The masked chip was then exposed to UV for 5 min and 30 s at 3.5 mW/cm$^2$, as measured with a UV513AB Digital Light Meter (General Tools, New York N.Y.). Unpolymerized material was evacuated and the precursor for the next binding gel region was introduced to the central chamber by applying vacuum at the adjacent reservoirs. Visual inspection of the chip channels and chamber was performed before each photopolymerization step to avoid introduction of air bubbles. If observed, bubbles within the channels or chamber were flushed out with a buffer solution via application of vacuum pressure and fresh PA gel precursor flushed in. When all requisite binding regions were polymerized, the unpolymerized binding gel precursor solution was evacuated from the central chamber and replaced with a 6% T PA separation gel solution.

The separation gel region was then masked to produce an interface near the top of the central chamber and exposed using the UV objective lens for 5 minutes at 3.5 mW/cm². Finally, the lower density loading gel precursor was flushed through the uppermost loading channels and the entire chip was exposed to a filtered mercury lamp (UVP B100-AP, Upland, Calif.) with cooling fan. The final polymerization step required flood exposure for 5 minutes at 9 mW/cm².

As described above, UV light was used to polymerize gel precursor solutions that were sequentially introduced into the central chamber. High spatial resolution (~20 μm) photolithography techniques were used to produce more complex gel structures in the chamber, which enabled multiplex assays. The multistep fabrication process yielded a device with discrete loading and separation gel zones, as well as n binding gel regions fabricated using n+2 UV exposure steps (where n corresponds to the desired number of protein targets). Total fabrication time was from 2 to 4 hours depending on the device complexity. Completed chips were stored for several weeks at 4° C. and fully submerged in an aqueous buffer solution. Although the binding regions were designed for single use, the interior gels can be dissolved by immersing chips overnight in a perchloric acid (66%): hydrogen peroxide (33%) bath, such that the glass chips may be reused.

D. Fluidic Access and Voltage Control.

To conduct the binding assay, a photopatterned chip was seated on an epi-fluorescence microscope stage and ~2 μL of sample was aliquoted directly into the sample loading reservoir. All other reservoirs were loaded with Tris-glycine buffer, and a platinum electrode was inserted into each. Continuous control and monitoring of voltage and current levels at each electrode was accomplished using an 8 channel high voltage power supply with current/voltage feedback control (see Table 1). Electrical field strengths within the device were estimated by dividing the difference in applied electrical potential by the distance between electrodes.

E. Data Collection and Analysis.

Image collection was performed with a CCD camera (CoolSNAP™ HQ2, Roper Scientific, Trenton, N.J.) and a 10× objective (UPlanFL, N.A.=0.3, Olympus, Center Valley, Pa.) using an inverted epi-fluorescence microscope (IX-70, Olympus). Camera exposure time was 300 ms and 2×2 pixel binning was employed, resulting in a full field image representing a ~1 mm×1.34 mm field of view. Use of full field imaging allowed all analytes to be simultaneously observed during protein separation and detected on antibody functionalized blotting regions after lateral transfer. Light from a mercury arc lamp was filtered through XF100-3 or XF111-2 filter sets (Omega Optical, Brattleboro, Vt.) for illumination of AlexaFluor 488 and 568 labeled proteins, respectively. Two color image composites were compiled from individual red and green wavelength image sequences taken during two different runs upon the same device. Identical conditions and timing were maintained and images from each color channel were synchronized to an electrical signal observed at the trigger of each experiment, then merged into a single sequence in post-processing via ImageJ (NIH, Bethesda, Md.).

Image analysis was performed using ImageJ and regions of interest (ROI) corresponding to the separation and blotting regions were selected and consistently applied. Line sections across the ROI were averaged to calculate the spatial distribution of the fluorescence signal. SR between protein bands was defined as SR=ΔL/4σ where ΔL is the distance between adjacent band centers and σ represents the average characteristic band width (assuming Gaussian distribution). Two analyte bands were resolved when SR>1. σ was calculated by applying a Gaussian peak fitting algorithm using OriginPro (OriginLab, Northampton Mass.).

F. Simulation of Analyte Capture in Blotting Regions.

Simulations were written and performed using Matlab (MathWorks, Natick Mass.).

III. Results and Discussion

A. On-Chip Multiplexed Native Western Blot.

Figure 2:
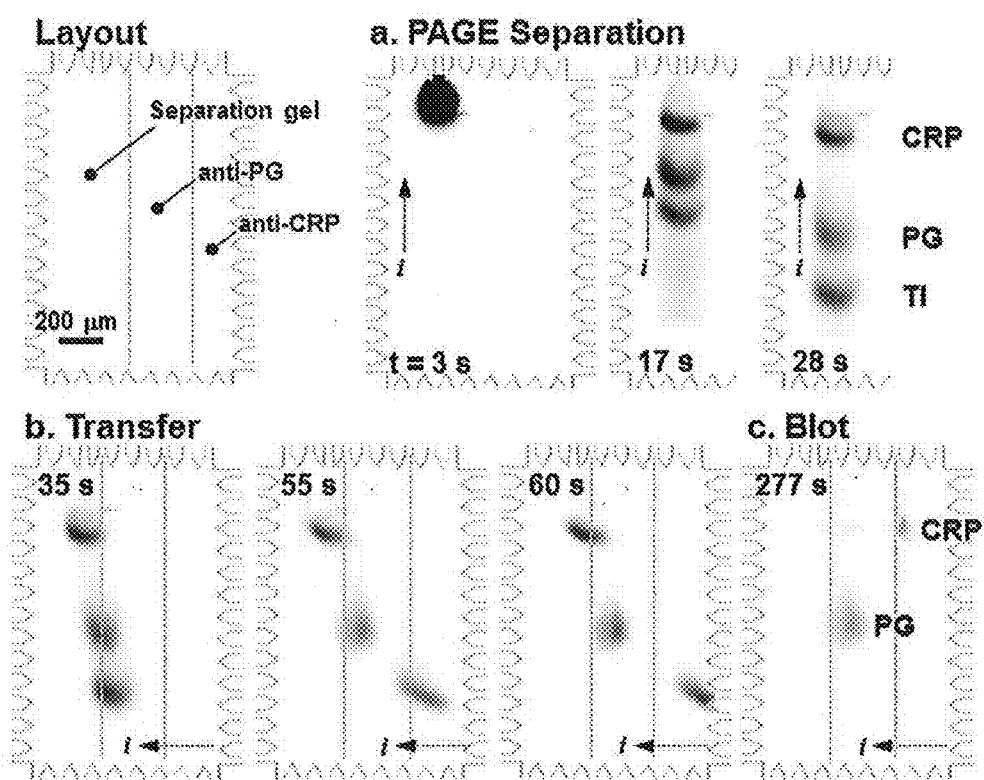
FIG. 2 shows a schematic of a microfluidic device with discrete blotting regions that enable (a) separation, (b) transfer, and (c) multiplexed blotting of unique targets from a single sample according to embodiments of the present disclosure. Negative control (TI) showed no interaction with the blotting regions or interfaces. E=95 V/cm during injection/separation, E=50 V/cm during transfer of separated proteins to the blotting regions. (Image collection via fluorescence microscopy)

To assess on-chip multiplexed re-blotting performance and establish a robust assay protocol, a fluorescently labeled three analyte ladder was assayed. The ladder consisted of two target proteins (CRP, PG) and a high electrophoretic mobility negative control (TI). Results from the protein blotting assay are shown in FIG. 2 with performance characterization of the three major steps (native PAGE separation, transfer, and multi-analyte blotting) described below.

Native PAGE.

To assess the injection dispersion minimization effect of the stacking gel, the standard deviation of the injected sample band was compared immediately before ($\sigma_{inj}$) and after passing through the stacking interface ($\sigma_{stack}$) within the microchamber. For the architecture used here, the presence of the stacking interface reduced injection dispersion by 75%, from $\sigma_{inj}$=117 μm to $\sigma_{stack}$=29 μm. Concomitantly, a 41%±19% (n=6) increase in the maximum of the fluorescence signal was observed when a band crossed the stacking interface. Upon passing through the stacking interface (separation time of t=17 s), the injected plug was resolved into PG ($\sigma_{PG}$=122 μm), TI ($\sigma_{TI}$=96 μm) and CRP ($\sigma_{CRP}$=96 μm). At t=17 s, all three species were baseline resolved, with an SR of 1.10 between TI/PG and 1.78 between PG/CRP. The separation occupied 630 μm of the 1290 μm separation axis (from stacking gel to TI peak center).

Electrophoretic Transfer to Binding Regions.

At t=28 s, electrophoretic sample transfer from the native PAGE separation axis to the binding regions was initiated. The separation electric field was switched off and an electric field was applied perpendicular to the separation axis to drive species across the separation chamber and to the binding regions. Regulation of current flow at control reservoirs 1, 5, 6, 7 and 8 (FIG. 1(*a*)) was employed to minimize fringing fields in the chamber, both during transfer (FIG. 2(*b*)) and during the prior separation (see voltage control program for details, Table 1).

Full band transfer to the blotting regions was completed within 25 s for the PG peak (high mobility positive control) and within 210 s for the lower mobility CRP peak. The high mobility negative control migrated through both binding regions and out of the 2D chamber within 50 s. The lateral electrotransfer was completed when the slowest species traversed the lateral span between the separation axis and last binding region. Changes in protein band width, peak positions and SR before and after sample transfer and binding are shown in Table 2. The average bandwidth decreased by an average of 16% (along the lateral dimension) after binding, as compared against the width of the band during PAGE.

Figure 7:
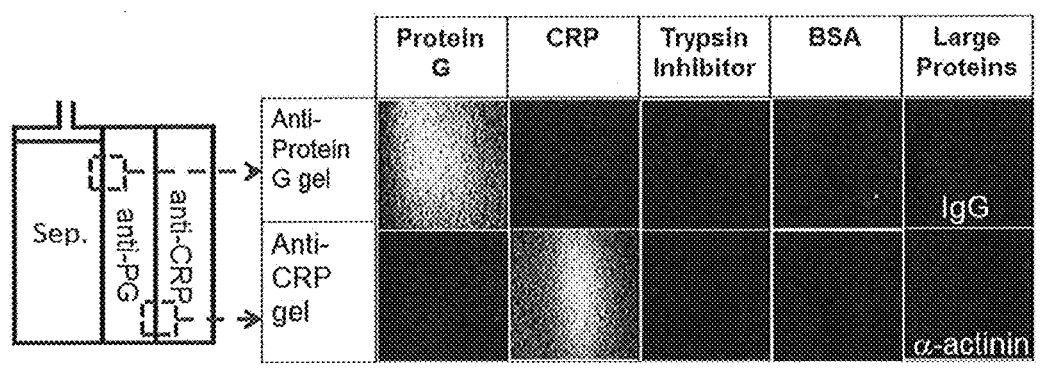
FIG. 7 shows post-transfer fluorescent microscope images taken at corresponding blotting regions within the device according to embodiments of the present disclosure. Large fluorescently labeled non-target molecules are not retained at the blotting gel interface due to pore size exclusion or non-specific binding interactions. Positive controls show up as green fluorescence distribution upon corresponding blotting regions (see Protein G v. anti-protein G gel and CRP v. anti-CRP gel). Negative controls include high molecular weight species such as α-actinin and IgG (100 and 150 kDa, respectively).

To assess non-specific exclusion (e.g., physical size exclusion) or retention at the blotting gel interfaces (i.e., separation-to-blotting region, blotting region 1-to-2) and within each blotting region, negative control proteins not specific to the antibody functionalized gel were monitored. FIG. 7 shows a matrix illustration of positive and negative control experiments to assess size exclusion effects at blotting gel interfaces. To study size exclusion effects at the gel region interfaces, large analytes including BSA (66 kDa), α-actinin (100 kDa) and IgG (150 kDa) were assessed against anti-CRP and anti-protein G antibody-functionalized blotting regions. During sample transfer, fluorescence at the blotting interface and within the blotting regions was monitored. The large negative control proteins passed through the blotting region without exhibiting a decrease in electrophoretic mobility as they crossed from the separation gel into and out of the blotting region. BSA and α-actinin samples, assayed at 300 nM, displayed 5% and 4% residual signal at the separation gel to anti-PG and anti-CRP interfaces after each respective peak migrated across the blotting region.

FIG. 7 shows the transport of large negative control proteins (ranging from 66-150 kDa) which were able to pass through the binding region. In the dual analyte assays, negligible change in electrophoretic mobility of the negative control protein (TI) was observed ($\mu_{TI}$ along separation axis: $4.93 \times 10^{-5}$ cm$^2$/Vs, in α-CRP region: $4.93 \times 10^{-5}$ cm$^2$/Vs; in α-PG region: $4.95 \times 10^{-5}$ cm$^2$/Vs). Negligible stacking and negligible de-stacking were observed at any gel interface in the lateral transfer direction (separation to blotting gel or between the two blotting regions) due to the closely matched pore-sizes both within the regions and at each lateral transfer interface.

TABLE 2

Band width, peak center position and separation resolution are maintained throughout lateral transfer.

| Analyte | Bandwidth (µm) | Variation | Peak Center Shift (µm)/% of Separation Axis | Separation Resolution ΔL/4δ | Variation |
|---|---|---|---|---|---|
| TI | 127 (before) 123 (after) | 3% | 14/1% | TI/PG 1.26 (before) 1.48 (after) | 18% |
| PG | 171 (before) 182 (after) | 7% | 29/2% | PG/CRP 2.28 (before) 2.22 (after) | 6% |
| CRP | 89 (before) 101 (after) | 14% | 53/4% | | |

Before: Imaged at 30 s. After: Imaged at 250 s. Peak center shift was defined as the net displacement of the peak center along the separation axis following lateral transport to the blotting region, and was also represented in relative proportion to the length of the separation axis.

Blotting and Fluorescence Readout.

The dual analyte native blot yielded a linear dose-response from 8 to 800 nM (y=0.042x−0.187; R$^2$=0.988, n=5), as measured via fluorescence imaging for the protein G sample. Plotting fluorescence intensity across the length of the protein band resulted in an area under the curve correlated to the total mass of protein capture. Comparisons of pre-blot and post-blot PG and CRP band measurements demonstrated that between 85 and 95% of each protein band was captured on the matching antibody functionalized binding regions. A lower limit of detection of 2.5 nM was established based upon a SNR of ~3 for the current standard epi-fluorescence based full field imaging system. The full field imaging capability was selected for use here, as it allowed for simultaneous quantitative measurement of multiple analytes, so that relative expression levels of these targets in one same sample may be compared within a single assay. Sub-nanomolar levels of sensitivity were possible with more sensitive detection approaches, such as a scanning laser/photomultiplier tube system.

B. Establishing Conditions for Analyte Blotting.

To establish optimal operating conditions for blotting, modeling of the immunoblotting process was performed. Assuming the interaction between migrating protein and immobilized antibody was sufficiently represented by a first order Langmuir binding model, the concentration distributions of bound ($C_{bound}$) and free target protein (C) can be expressed as a binding reaction and a differential equation:

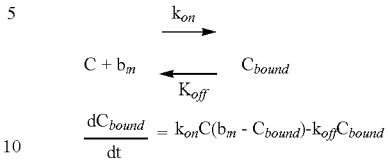

$$\frac{dC_{bound}}{dt} = k_{on}C(b_m - C_{bound}) - k_{off}C_{bound}$$

Here, $b_m$ represented available binding sites on the immobilized antibody population. Free analyte binding at a binding site was governed by a forward association rate constant $k_{on}$ (M$^{-1}$ s$^{-1}$) and a backward disassociation rate constant $k_{off}$ (s$^{-1}$). For this system, the non-dimensional Damköhler number (Da) represented the ratio of reactive flux (determined by $k_{on}$ and availability of binding sites) to the mass transport flux (electromigration). Specifically, Da=(L$k_{on}b_m$)/$U_o$ where L was the width of the blotting region and $U_o$ represented the analyte electromigration speed through the blotting region. Here, $U_o = \mu_o E$, where E was the applied lateral electric field strength and $\mu_o$ represented the electrophoretic mobility of the analyte, such that: Da=(L$k_{on}b_m$)/$\mu_o E$. Thus, Da described the relationship between two timescales: electromigration time (L/$\mu_o E$) and binding reaction time (1/$k_{on}b_m$). To provide context, when the value of Da was high (>10), the duration of protein target co-localization in the binding gel significantly exceeded the characteristic timescale necessary for a binding reaction. Thus, the system was mass transport limited. At low Da (<1), the target moved through the binding region too quickly for binding to occur and the system was reaction limited. Operating in the mass transport limited regime (Da>10), while maintaining a reasonable total assay time as defined by the application, was desired.

Figure 8:
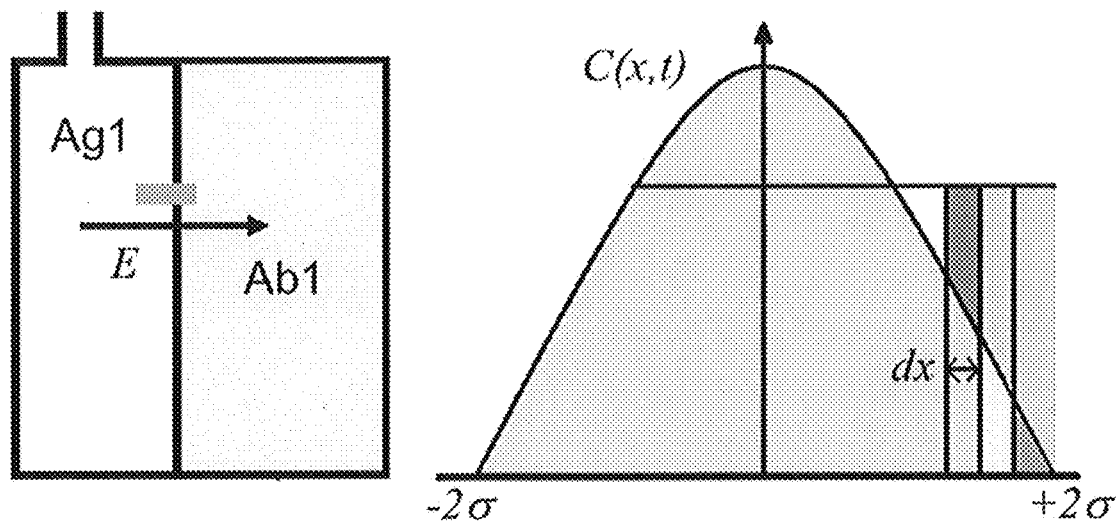
FIG. 8 shows that the proposed model simulates Langmuir binding reactions between two sets of differential elements over a series of finite intervals according to embodiments of the present disclosure. The migration speed determines a residence time step ($\Delta t$) wherein each target band element is co-localized or "incubated" with a matching gel element.

Both the depletion of target band ($\Delta C_{bound}$) and the spatial distribution of bound target within the blotting gel ($C_{bound}$) were modeled for a single target-band, single blotting-region system. Here, x corresponded to the lateral (transfer) axis of the microchamber. The migrating protein band was modeled in one dimension as a Gaussian distribution with width from −2σ to +2σ. The concentration distribution was divided into a series of n differential elements of equal width ΔX. Each band element was assigned an initial concentration value C(x,$t_o$). The binding region was similarly represented by p gel elements of equal width ΔX, such that p=L/ΔX, where L represents the total length of the blotting region (FIG. 8).

Electrophoretic migration speed determined a residence time step (Δt) where each target band element was co-localized or "incubated" with a matching binding gel element. The average peak migration speed through the binding gel was assumed to be constant and uniform over all binding regions. For each time step, the bound protein concentration was expressed by:

$$\Delta C_{bound} = (k_{on}C(b_m - C_{bound}) - k_{off}C_{bound})\Delta t$$

TABLE 3

Simulation parameters, both empirical and a priori determined.

| Variable [units] | Range | Experimental | Simulation |
|---|---|---|---|
| $b_m$ [µM]' | 0-22 | 1.6* | 1.6 |
| E [V/cm] | 10-150 | 50-75 | 50 |
| L [µm] | 20-500 | 100-300 | 100-200 |

TABLE 3-continued

Simulation parameters, both empirical and a priori determined.

| Variable [units] | Range | Experimental | Simulation |
|---|---|---|---|
| $k_{on}$ [M$^{-1}$s$^{-1}$] | $10^4$-$10^8$ | — | $5.75 \times 10^5$ |
| $k_{off}$ [s$^{-1}$] | $10^{-1}$-$10^{-5}$ | — | $1 \times 10^{-3}$ |
| $\mu_o$[cm$^2$/Vs] | $1$-$7 \times 10^{-5}$ | $6.6 \times 10^{-5}$ | $6.6 \times 10^{-5}$ |
| $\sigma$ [µm] | 10-100 | 80 | 80 |
| C [nM] | 1-500 | 8-1250 | 800 |

*Assuming full binding site availability

After each time step, the calculated $\Delta C_{bound}$ was subtracted from the corresponding band and gel elements. Note that timescales for $k_{off}$ were typically $10^7$-$10^{10}$ larger than that of $k_{on}$. In the simulation, the band was allowed to advance relative to the gel, and the next set of band/gel incubation steps was computed. Empirically determined electrophoretic mobility values and known sample/antibody concentrations were used (Table 3).

Figure 3:
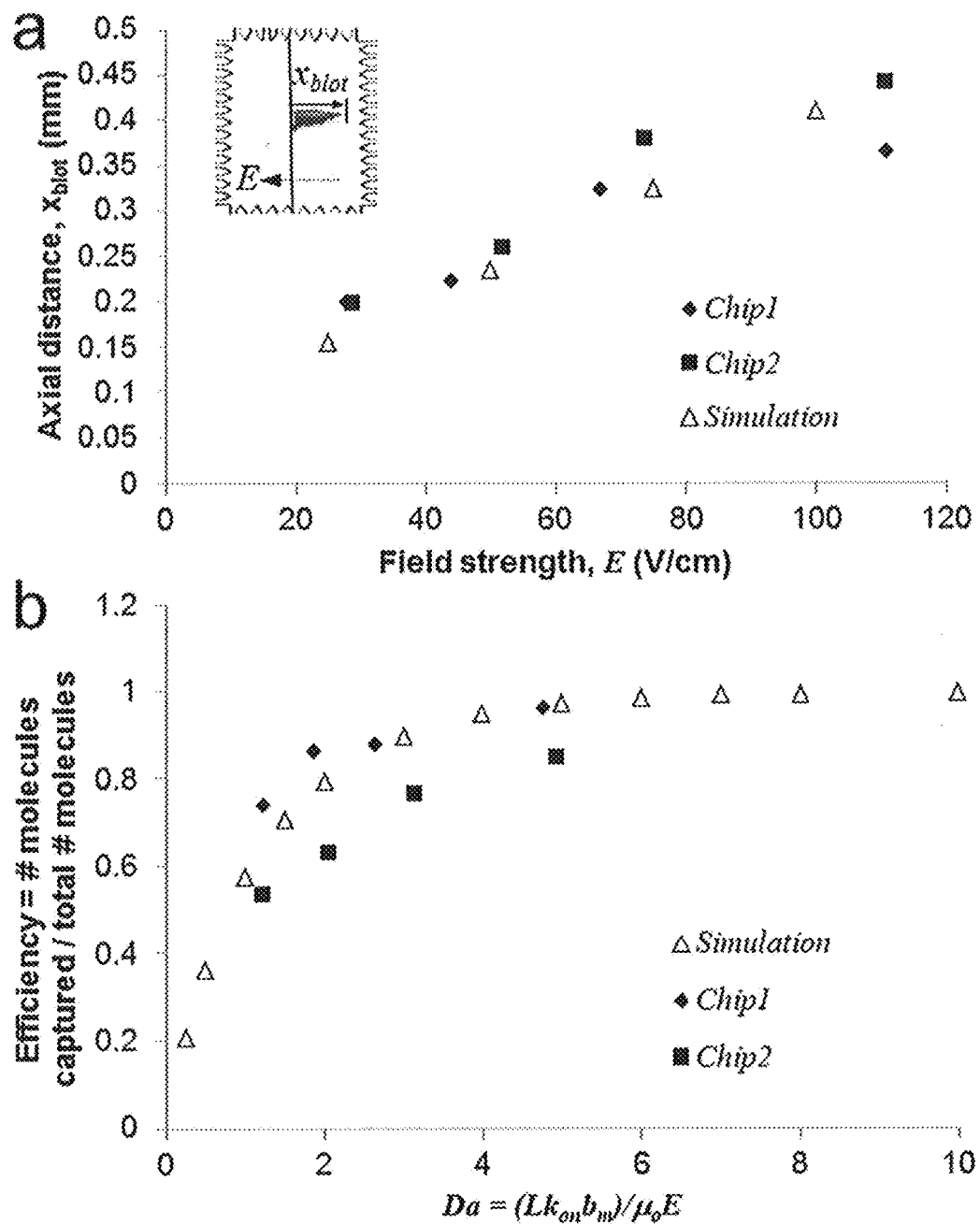
FIG. 3 shows graphs related to the modeling of binding in blotting regions, which informs selection of operating conditions to maximize binding efficiency, according to embodiments of the present disclosure.

Selection of an appropriate $k_{on}$ was critical in fitting the model, as $k_{on}$ was the only parameter which cannot be directly extracted from empirical observation and system design. Values for $k_{on}$ can vary by several orders of magnitude depending upon the antigen/antibody pair and local microenvironment. While the present model does not capture the full convection-diffusion behavior of the band, band migration through the blotting region was relatively short when compared to the transfer and separation period, thus substantiating neglect of diffusive effects in the blotting gel during binding interactions. FIG. 3 compares results obtained from simulation to experimental results in which an 800 nM PG sample was transferred to an α-PG blotting gel at specified lateral field strengths. Here, the length of the immobilized band was defined as the distance from the separation/blotting gel interface that contains 90% of the total area-under-curve when bound antigen concentration was plotted as a function of space. In simulation and in experimental work, the length of the blotting region required for full antigen capture increased linearly as a function of applied field strength. A 500 µm lateral distance was sufficient for total capture of this antigen, even for a high concentration target in lateral fields of greater than 100 V/cm (FIG. 3(a)).

FIG. 3(b) illustrates how variations in binding efficiency were influenced by parameters such as field strength and sample properties. Assuming a blotting region width of 100 µm and a binding site density of 1.6 the values for E are varied from 14-140 V cm$^{-1}$, $\mu_o$ was varied from 2-40 cm$^2$ V$^{-1}$ s$^{-1}$ and $k_{on}$ was varied from 0.5-20 M$^{-1}$ s$^{-1}$. Binding efficiency was used as a metric of target capture. If the width of the blotting region was less than the requisite dimensions of the full immobilized band, the efficiency of protein capture may be sub-optimal. The model detailed here was useful for optimizing performance and informing device design.

Knowledge of the minimum blotting gel width for a specific set of operating (i.e., E, L) and analyte characteristics (i.e., antigen/antibody binding affinities, analyte mobility) was helpful in maximizing the capacity of a multi-analyte blotting assay. Based upon the requisite lengths of the lateral transfer regions under current conditions, it was estimated that blotting against 8-10 antibodies was possible with further expansion of the central chamber. Specifically, the model aided in device design for biological applications where the electrophoretic mobility and binding affinity constants may range widely for species in one multi-analyte sample. When experimental results were compared against simulations, the spatial distribution of an immobilized band can also serve as a basis for estimating previously unknown binding affinities.

In some cases, it may be advantageous to lower the strength of the lateral electric field, thus prolonging the time in which the antigen target was co-localized to the capture antibody during sample transfer. This increased "incubation time" resulted in a higher capture efficiency and enhanced the localized binding signal which determined the limit of detection. However, a slower transfer speed could also result in greater band dispersion. Alternatively, one could also increase the local capture antibody concentration to minimize the requisite lateral trapping length and increase measurement sensitivity. On-chip arrangement of various antibody functionalized regions can be customized depending upon the transfer behavior of the analytes. For example, cross reactivity between antibodies for multiple species within a single sample can often present an obstacle to all forms of immunoassay. In cases where known cross reactivity exists between binding antigen/antibody pairs, the sequence of antibody functionalized blotting regions within a 2D chip can be specified to minimize ambiguous or spurious measurements. Note that blotting region widths need not be identical for all target species.

C. Blotting of Co-Migrating Species as Relevant to Analysis of Protein Isoforms.

Figure 4:
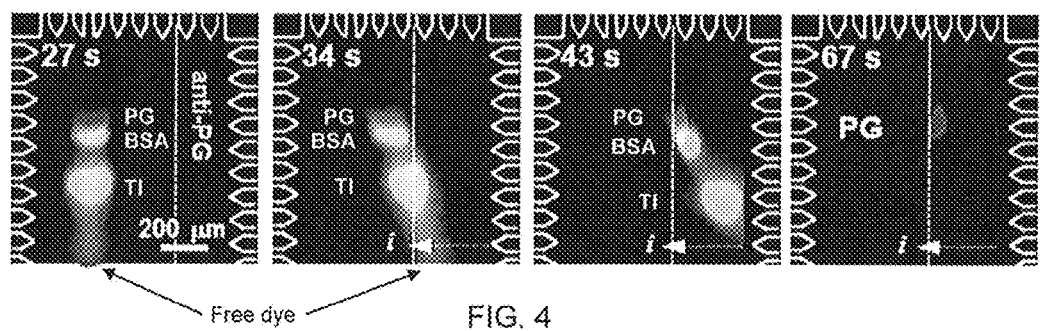
FIG. 4 shows images showing that protein immunoblotting enabled selective protein blotting for co-migrating species according to embodiments of the present disclosure. Two color image composite shows native PAGE (27 s) with two co-migrating species, here red labeled protein G (PG) and green labeled BSA. Green labeled TI acted as a fast moving negative control. Fastest red peak was free dye. Lateral transfer moved all species to the single blotting region (34 s and 43 s), housing immobilized antibodies against protein G. Red labeled protein G was selectively bound while both BSA and TI migrated out of the chamber (67 s).

In conventional blotting assays, stripping and re-blotting of the blotting membranes (i.e., PVDF or nitrocellulose sheet) may be the only option when two antigens exhibit closely matched electrophoretic velocities. For example, this may occur in studies of isoforms or post-translational modifications of a protein which result in relatively small differences in molecular weight. On-chip blotting was assessed as a means to selectively blot and identify one of two co-migrating species from native PAGE. Two-color imaging data presented in FIG. 4 shows native PAGE analysis of a sample comprised of fluorescently labeled PG target (red fluorescent label) and a sample ladder composed of BSA and TI (green fluorescent label). The PG band displayed an electrophoretic velocity which differs by 10% from BSA, thus species co-migrate early in the native PAGE assay.

At an elapsed PAGE separation time of t=27 s, the electric field was switched to the lateral direction and all species migrated to the binding region located at chamber right. Transfer at 50 V/cm required 38 s. Upon binding against an α-PG antibody immobilized in the binding region, the red-labeled PG was specifically retained in the α-PG binding region. Binding efficiency, defined as: # molecules bound/total # molecules (based upon fluorescence intensity measurement), was estimated at 95% for PG. All non-target bands migrated through the blotting region (t=30 to 65 s) with no detectable fluorescent signal, leaving behind the captured antigen of interest. The immunoblot was completed 65 s after sample injection.

D. Label Free Detection on the Blotting Regions.

To yield label free on-chip native Western blotting, all assay steps proceeded as described earlier with exceptions being: 1) the protein sample was no longer fluorescently labeled prior to PAGE and 2) a fluorescently labeled detection antibody was introduced after analyte capture on the blotting region. Here, the assay was demonstrated for PG at 500 nM. To more clearly illustrate the assay concept, PG was labeled with a green fluorophore (detection antibody was labeled with red). In practice, the sample proteins would not be labeled but a dye-labeled protein ladder could be included with the sample as a relative mobility reference.

Figure 5:
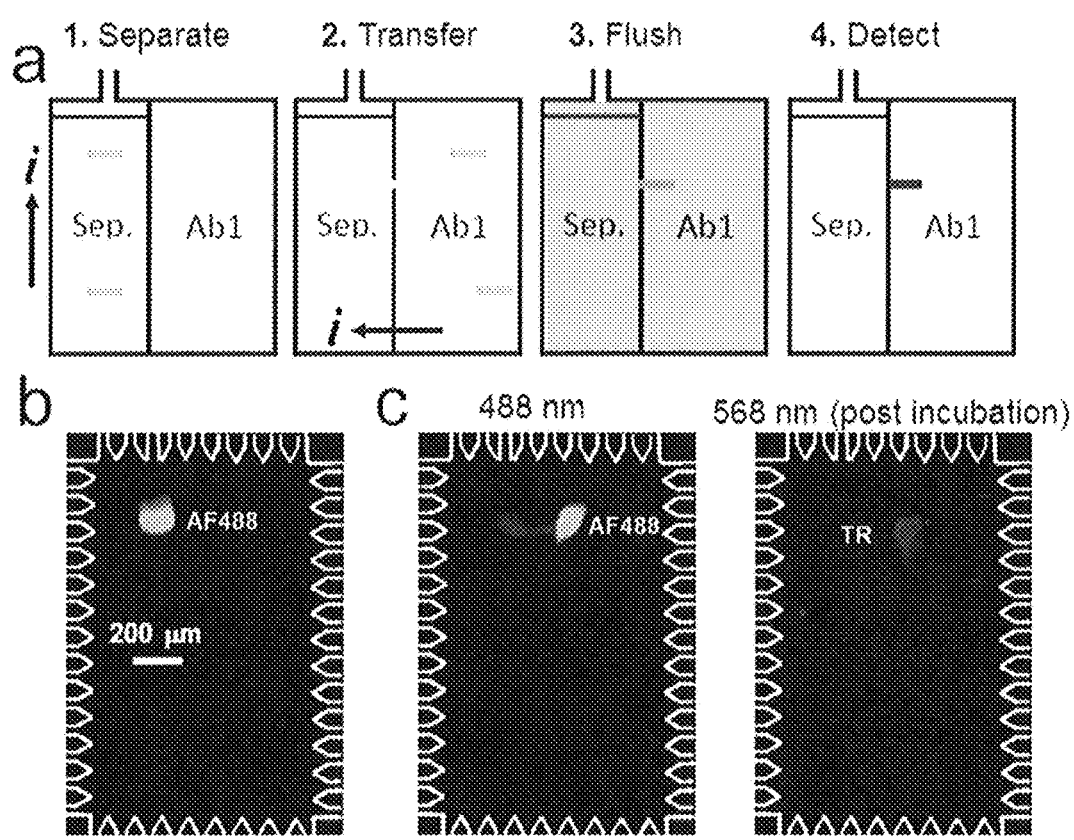
FIG. 5 shows a sandwich assay that allowed for detection of an unlabeled sample (SNR ~38), according to embodiments of the present disclosure.

After sample capture, fluorescently-labeled detection antibody (6 μM) matched to the bound target was introduced to the binding region from the control channel array at device right (E=150 V/cm). The detection antibody was then electrophoretically flushed out of the binding/separation chamber after a 20 min incubation period. As observed in FIG. 5, the detection antibody reported a fluorescence signal (red, SNR ~39) at the position of the immobilized target protein band on the blotting region (as illustrated in green). The approach was also compatible with enzyme-linked amplification to further enhance the detection signal upon the blotting region.

IV. Summary and Conclusions

The experiments above demonstrated an integrated assay that reports 1) analyte electrophoretic mobility obtained via native PAGE with 2) subsequent antibody-based blotting of multiple species. A microfluidic device was used for automated operation of re-blotting assays suitable for analyte quantitation. An analytical model was also developed that captures the competition between analyte electromigration and affinity based analyte capture in a gel binding regions. The model was used to inform device design (e.g., lateral dimension of binding regions and the maximum number of possible binding regions for the geometry described here) and selection of assay operating conditions (e.g., electrotransfer field strength) for optimum protein binding efficiency. Experiments were also performed where a multi-stage sample and reagent delivery protocol was used for a label free assay that used a sandwich antibody detection approach. Multispectral detection and enzyme amplification can be employed for multiplexing and to increase analytical sensitivity. The multiplexed immunoblotting technology described here for native protein analysis was demonstrated for both well resolved and not resolved proteins (from PAGE) and yielded total automated assay completion on the order of minutes.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device for detecting two or more analytes in a fluid sample, wherein the microfluidic device comprises:
 a chamber containing a contiguous monolith comprising:
  a loading medium;
  a separation medium, wherein the loading medium and the separation medium have a first flow field along a first directional axis and are arranged in series along the first directional axis;
  two distinct binding regions comprising:
   a first binding region comprising a first binding medium including a first binding member; and
   a second binding region comprising a second distinct binding medium including a second distinct binding member, and
   wherein the first binding region and the second binding region have a directionally distinct second flow field along a second directional axis and are arranged in series along the second directional axis; and
a flow field element configured to subject the chamber to the directionally distinct first and second flow fields.

2. The microfluidic device according to claim 1, wherein the directionally distinct flow fields comprise directionally distinct electric fields.

3. The microfluidic device according to claim 2, wherein the directionally distinct electric fields are orthogonal electric fields.

4. The microfluidic device according to claim 1, wherein the separation medium comprises a polymeric gel.

5. The microfluidic device according to claim 1, wherein the chamber further comprises a stacking medium in contact with the separation medium.

6. The microfluidic device according to claim 1, wherein the first binding medium is positioned between the separation medium and the second binding medium.

7. The microfluidic device according to claim 1, wherein the first and second binding members are stably associated with a polymeric gel.

8. The microfluidic device according to claim 7, wherein the binding member comprises a protein or a binding fragment thereof.

9. The microfluidic device according to claim 8, wherein the protein is an antibody.

10. The microfluidic device according to claim 1, wherein the two or more analytes are not labeled.

11. A method of assaying a fluid sample for two or more analytes, the method comprising:
(a) introducing the fluid sample into a microfluidic device comprising:
(i) a chamber containing a contiguous monolith comprising:
a loading medium;
a separation medium, wherein the loading medium and the separation medium have a first flow field along a first directional axis and are arranged in series along the first directional axis;
two distinct binding regions comprising:
a first binding region comprising a first binding medium including a first binding member; and
a second binding region comprising a second distinct binding medium including a second distinct binding member, and
wherein the first binding region and the second binding region have a directionally distinct second flow field along a second directional axis and are arranged in series along the second directional axis; and
(ii) a flow field element configured to subject the chamber to the directionally distinct first and second flow fields;
(b) directing the sample through the separation medium to produce a separated sample;
(c) directing the separated sample through the first and second binding mediums; and
(d) evaluating the first and second binding mediums for the presence of the two or more analytes.

12. The method according to claim 11, wherein the directionally distinct flow fields comprise directionally distinct electric fields.

13. The method according to claim 12, wherein the chamber further comprises a stacking medium and the method further comprises concentrating the sample prior to directing the sample through the separation medium.

14. The method according to claim 13, wherein the method further comprises flowing first and second labeling agents through the first and second binding mediums prior to evaluating the first and second binding mediums for the presence of the two or more analytes.

15. The method according to claim 12, wherein the method is a diagnostic method.

16. A system for assaying a fluid sample for the presence of two or more analytes, the system comprising:
(a) a microfluidic device comprising:
(i) a chamber containing a contiguous monolith comprising:
a loading medium;
a separation medium, wherein the loading medium and the separation medium have a first flow field along a first directional axis and are arranged in series along the first directional axis;
two distinct binding regions comprising:
a first binding region comprising a first binding medium including a first binding member; and
a second binding region comprising a second distinct binding medium including a second distinct binding member, and
wherein the first binding region and the second binding region have a directionally distinct second flow field along a second directional axis and are arranged in series along the second directional axis; and
(ii) a flow field element configured to subject the chamber to the directionally distinct first and second flow fields; and
(b) a detector.

17. The system according to claim 16, wherein the detector is a photomultiplier tube, a charge-coupled device, an intensified charge-coupled device, a complementary metal-oxide-semiconductor sensor, visual colorimetric readout, or a photodiode.

18. The system according to claim 16, further comprising microfluidic components configured to direct a fluid through the microfluidic device.

19. A kit comprising:
(a) a microfluidic device comprising:
(i) a chamber containing a contiguous monolith comprising:
a loading medium;
a separation medium, wherein the loading medium and the separation medium have a first flow field along a first directional axis and are arranged in series along the first directional axis;
two distinct binding regions comprising:
a first binding region comprising a first binding medium including a first binding member; and
a second binding region comprising a second distinct binding medium including a second distinct binding member, wherein the first binding region and the second binding region have a directionally distinct second flow field along a second directional axis and are arranged in series along the second directional axis; and
(ii) a flow field element configured to subject the chamber to the directionally distinct first and second flow fields; and
(b) a buffer.

20. The kit according to claim 19, wherein the kit further comprises first and second labeling reagents that respectively specifically bind to first and second analytes.

21. The microfluidic device according to claim 1, wherein the loading medium is in contact with the separation medium.

22. The microfluidic device according to claim 1, wherein the first binding medium and second binding medium are positioned such that the fluid sample flows from the first binding medium to the second binding medium along the second directional axis.

23. The microfluidic device according to claim 1, wherein the second binding medium is not in direct fluid communication with the separation medium.

24. The microfluidic device according to claim 1, wherein the contiguous monolith comprises a contiguous polymeric gel monolith.

25. The microfluidic device according to claim 1, wherein the separation medium and the first binding medium are in direct physical contact with each other, such that the analytes can traverse directly from the separation medium to the first binding medium.

26. The microfluidic device according to claim 1, wherein the separation medium is cross-linked with the first binding medium.

27. The microfluidic device according to claim 1, wherein the loading medium is cross-linked with the separation medium.

28. The microfluidic device according to claim 1, wherein the first binding member is immobilized in the first binding medium.

29. The microfluidic device according to claim 1, wherein the second binding member is immobilized in the second binding medium.

* * * * *